United States Patent [19]

Kurane et al.

[11] Patent Number: 5,175,279
[45] Date of Patent: Dec. 29, 1992

[54] POLYSACCHARIDE, AND WATER ABSORBENT, MOISTURE ABSORBENT OR HUMECTANT AND THICKENING AGENT CHIEFLY MADE OF THE POLYSACCHARIDE

[75] Inventors: Ryuichiro Kurane, Chiba; Tomoo Suzuki, Ibaraki; Yasuhiro Nohata, Mie, all of Japan

[73] Assignees: Hakuto Co., Ltd.; Agency of Industrial Science and Technology, both of Tokyo, Japan

[21] Appl. No.: 735,633

[22] Filed: Jul. 25, 1991

Related U.S. Application Data

[63] Continuation-in-part of Ser. No. 469,076, Jan. 19, 1990, abandoned.

[30] Foreign Application Priority Data

Jan. 19, 1989 [JP] Japan .................................. 1-10398
Jan. 8, 1990 [JP] Japan .................................. 2-1359

[51] Int. Cl.⁵ .......................... C07H 1/00; C07H 3/00; C08B 37/00; C12P 1/00
[52] U.S. Cl. .................................... 536/123; 536/1.1; 435/41; 435/829
[58] Field of Search ................... 536/123, 1.1; 435/41, 435/829

[56] References Cited

U.S. PATENT DOCUMENTS 4,454,316 6/1984 Veeder et al. ...................... 536/123

FOREIGN PATENT DOCUMENTS 23397 2/1981 European Pat. Off. .
64354 11/1982 European Pat. Off. .
2058106 4/1981 United Kingdom .
2058107 4/1981 United Kingdom .

Primary Examiner—Johnnie R. Brown
Assistant Examiner—Everett White
Attorney, Agent, or Firm—Fitch, Even, Tabin & Flannery

[57] ABSTRACT

A polysaccharide (Biopolymer B-16) being produced by cultivating Alcaligenes latus strain B-16 (FERM-2015) and having at least one function selected from water absorption, moisture absorption, humectant capability, thickening capability, suspension stability, emulsion stability and dispersant capability along with high biodegradability and which can be used without creating any environmental hazard such as secondary pollution, said Biopolymer B-16 consisting essentially of rhamnose, fucose, glucose, mannose and glucuronic acid which are present in a molar ratio of (1–10):(2–10):(4–20):(1):(1–5).

3 Claims, 17 Drawing Sheets

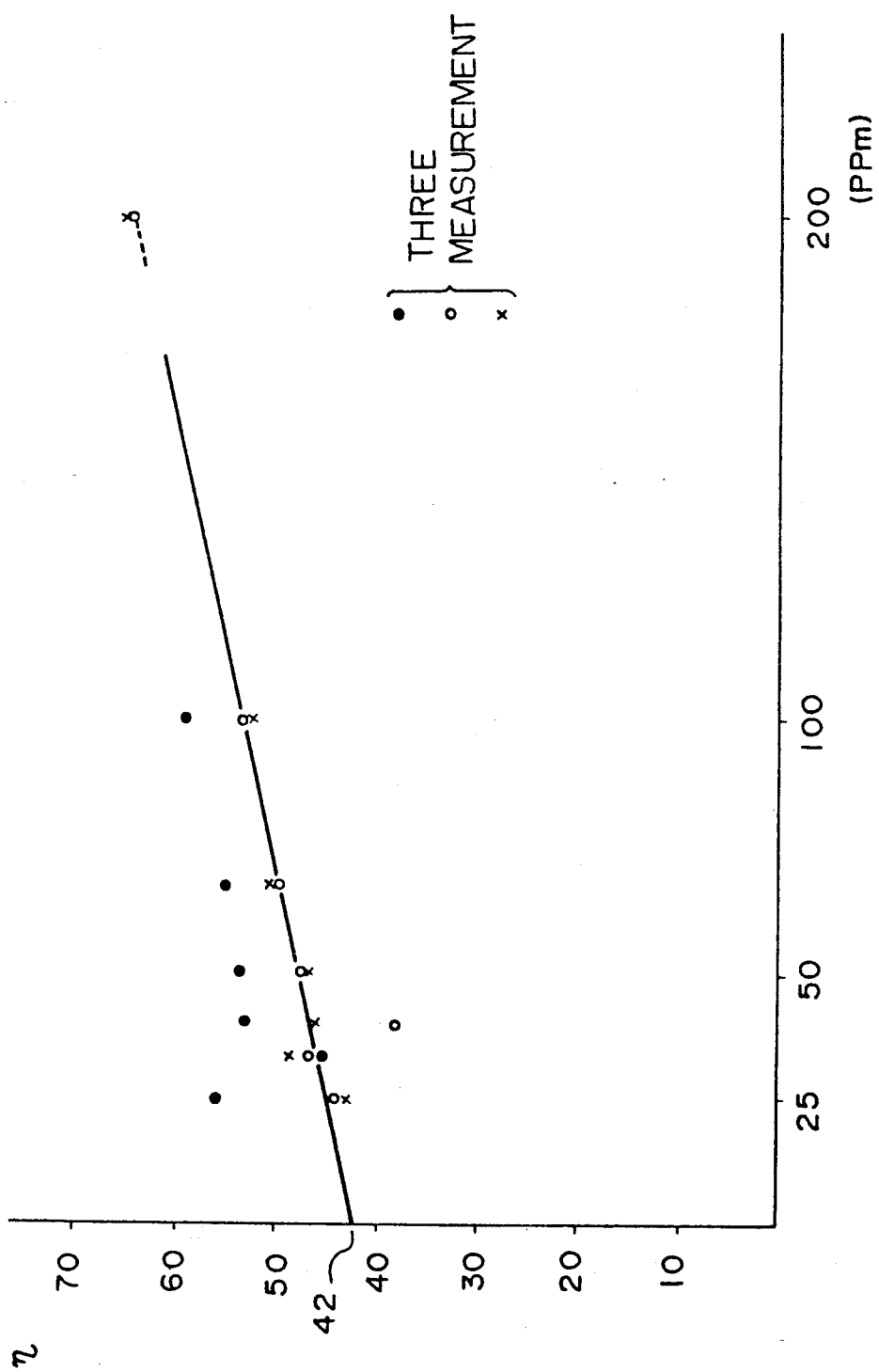

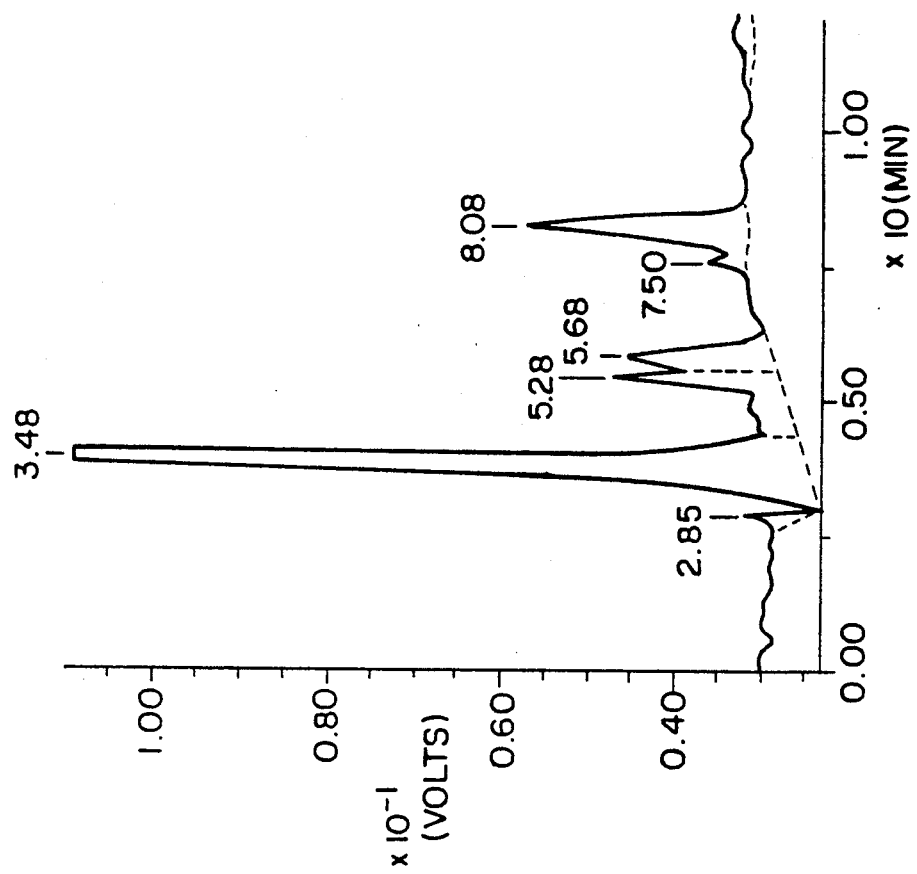
FIG. 4-B
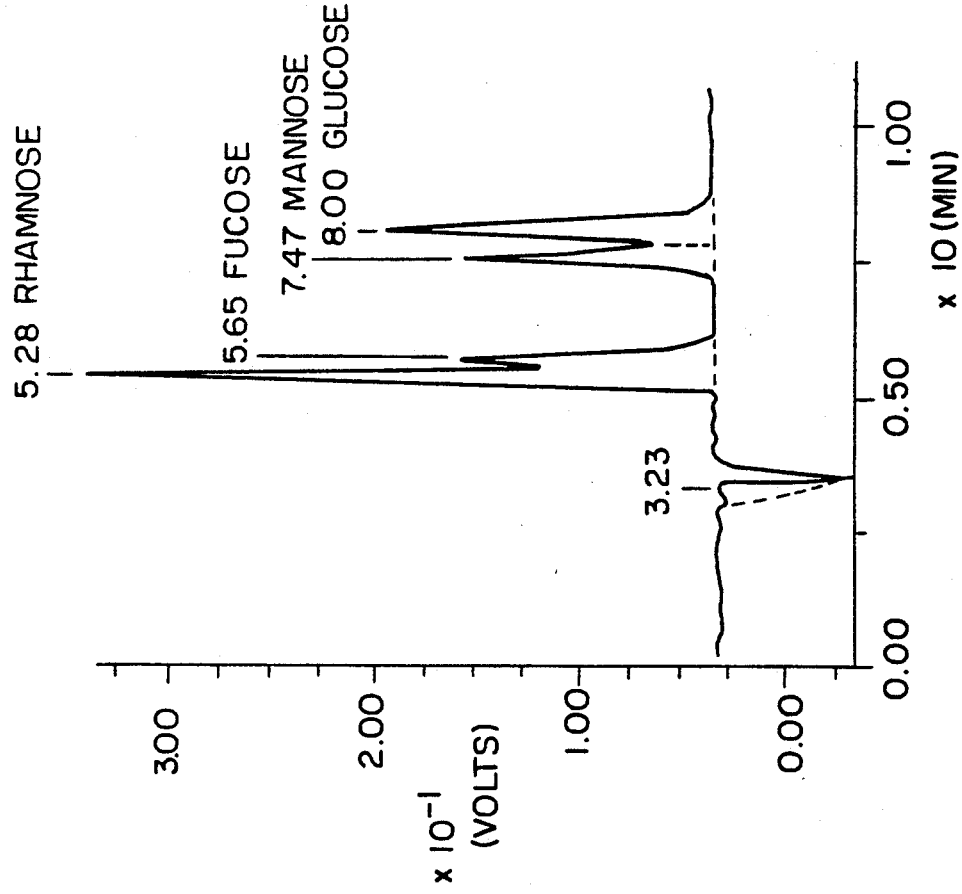
FIG. 4-A

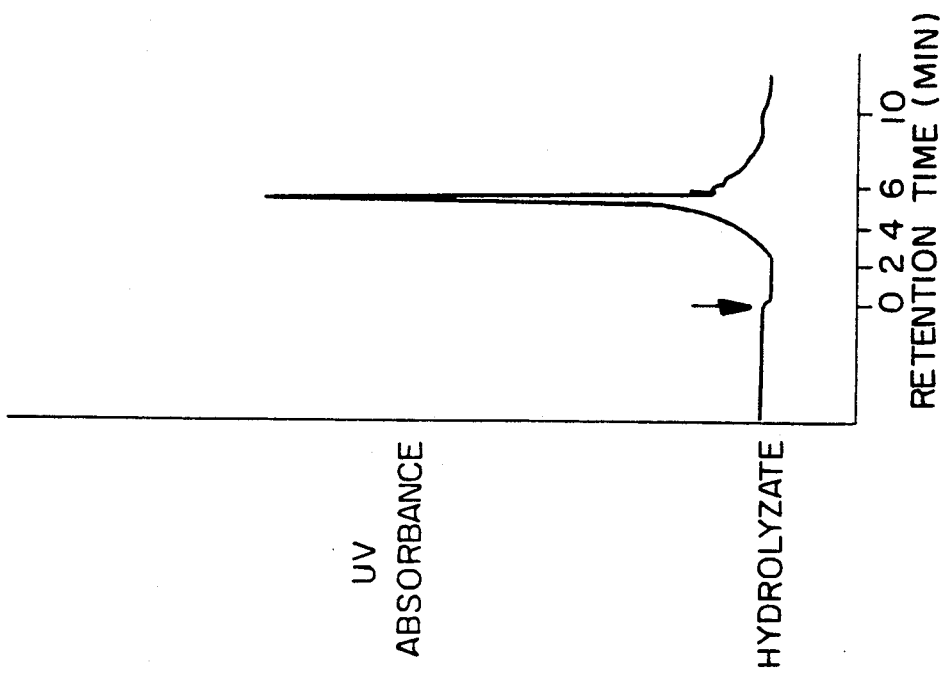
FIG. 4-C
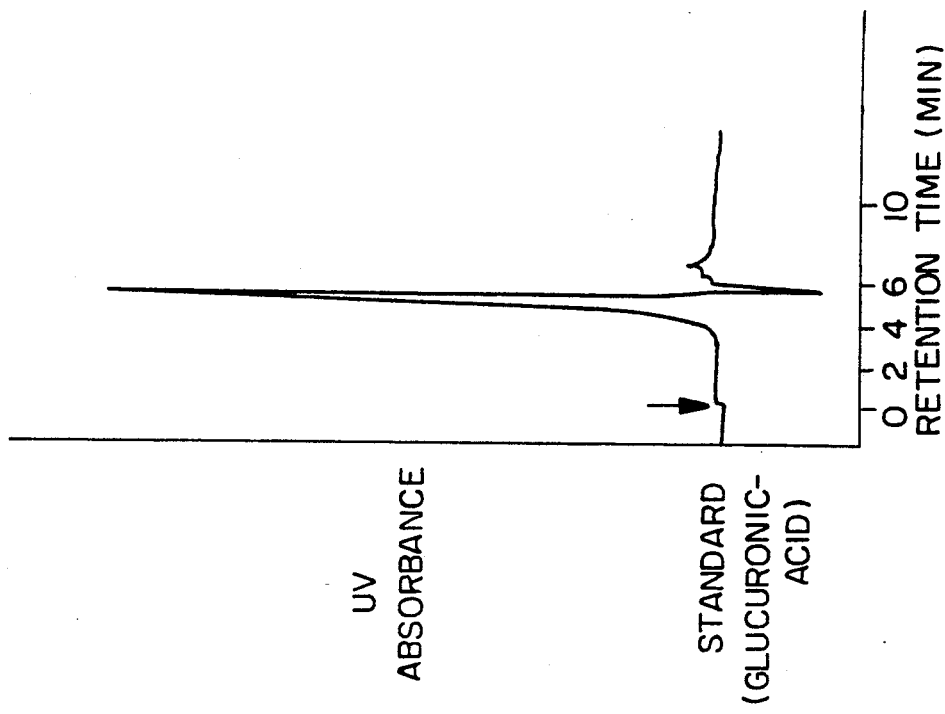
FIG. 4-D

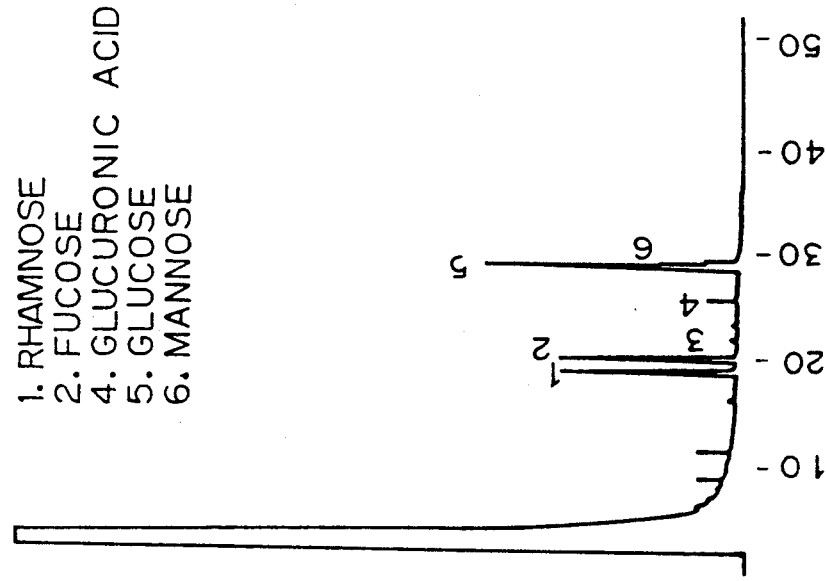
Fig.5-A
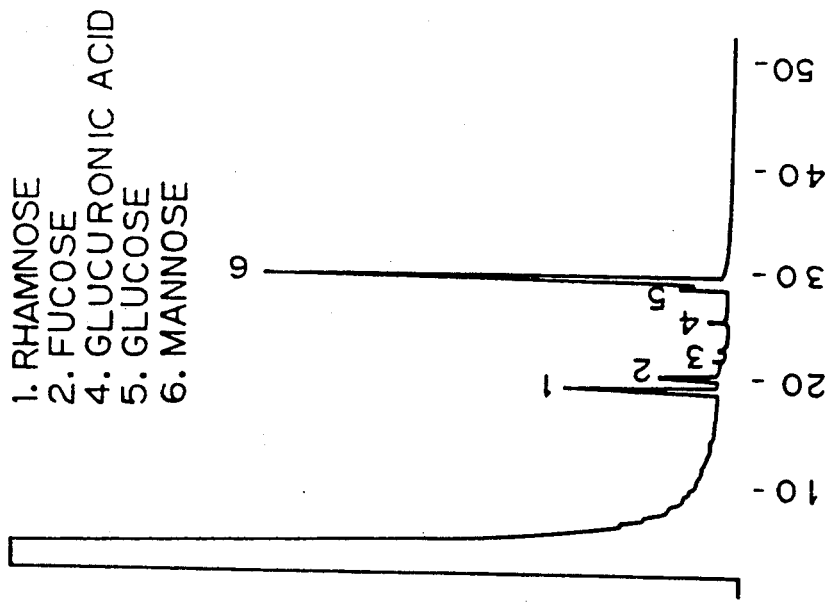
Fig.5-B

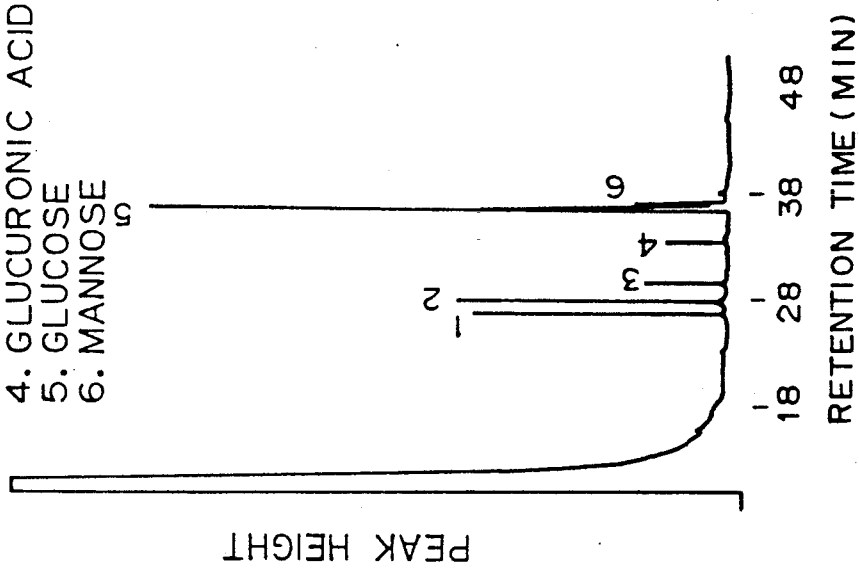
Fig. 7-A
1. RHAMNOSE
2. FUCOSE
4. GLUCURONIC ACID
5. GLUCOSE
6. MANNOSE
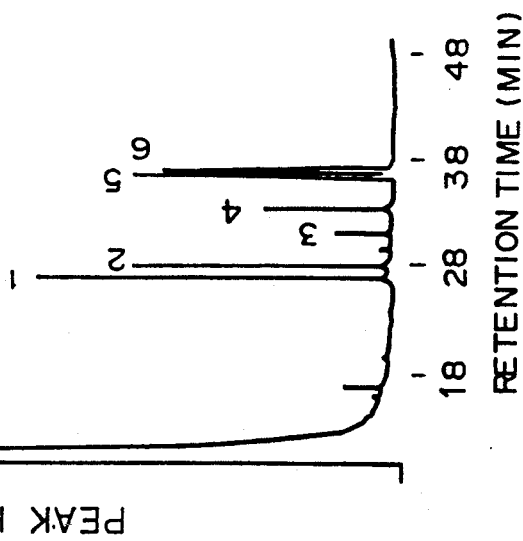
Fig. 7-B
1. RHAMNOSE
2. FUCOSE
4. GLUCURONIC ACID
5. GLUCOSE
6. MANNOSE

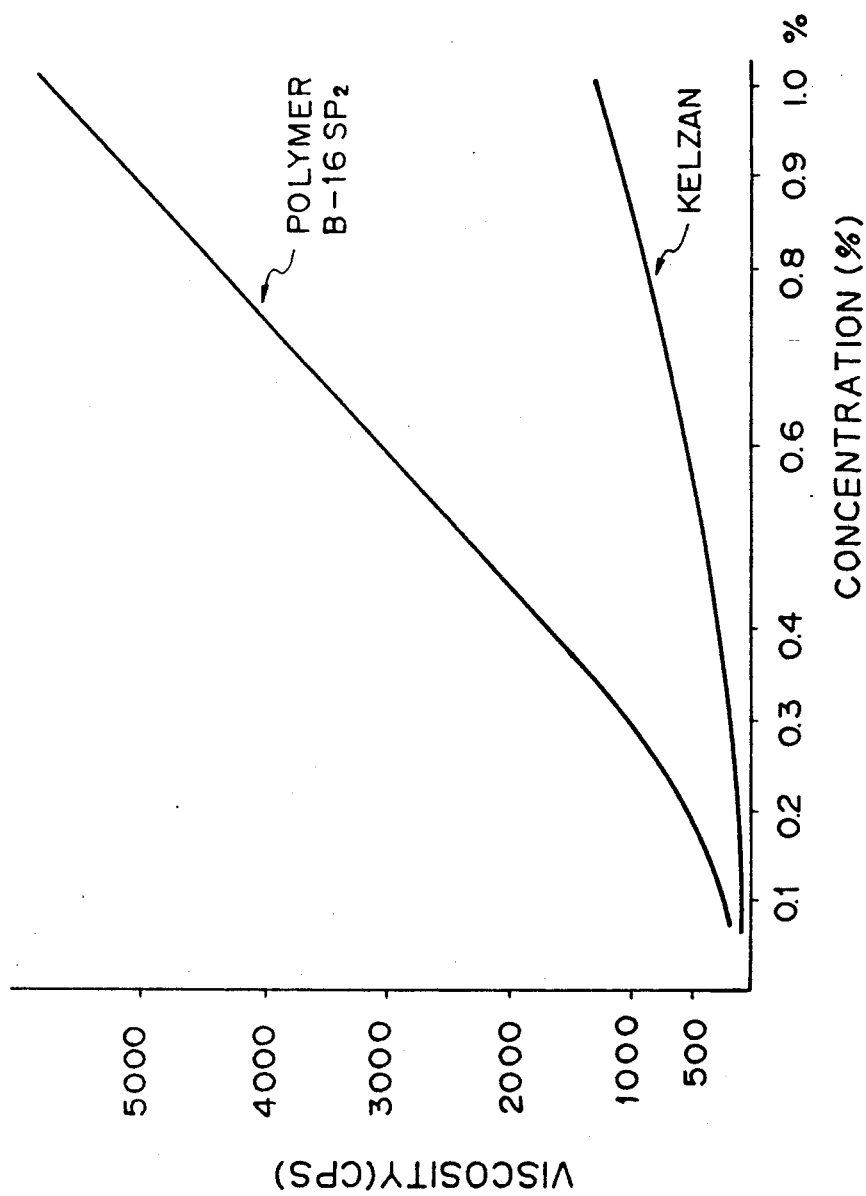

Fig. 10-A
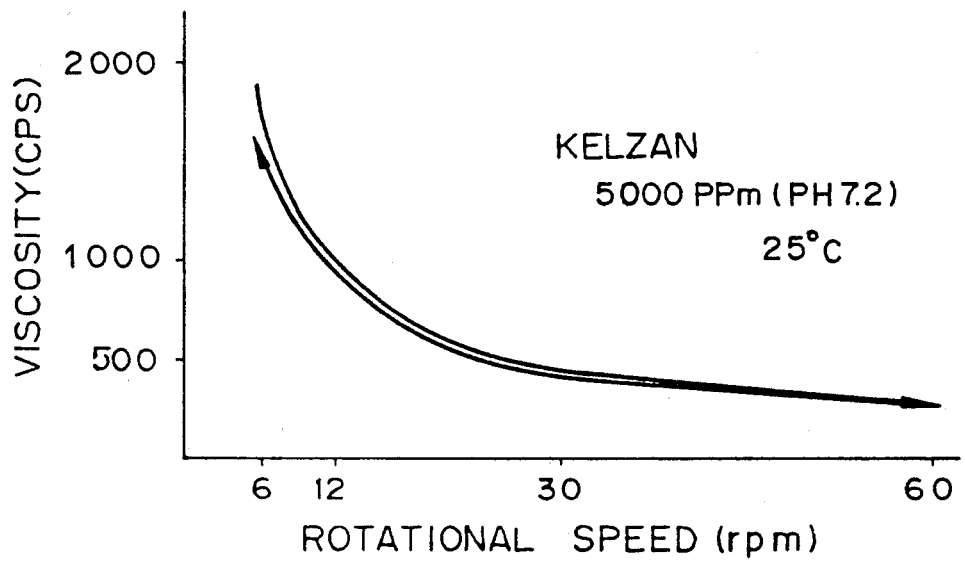
Fig. 10-B
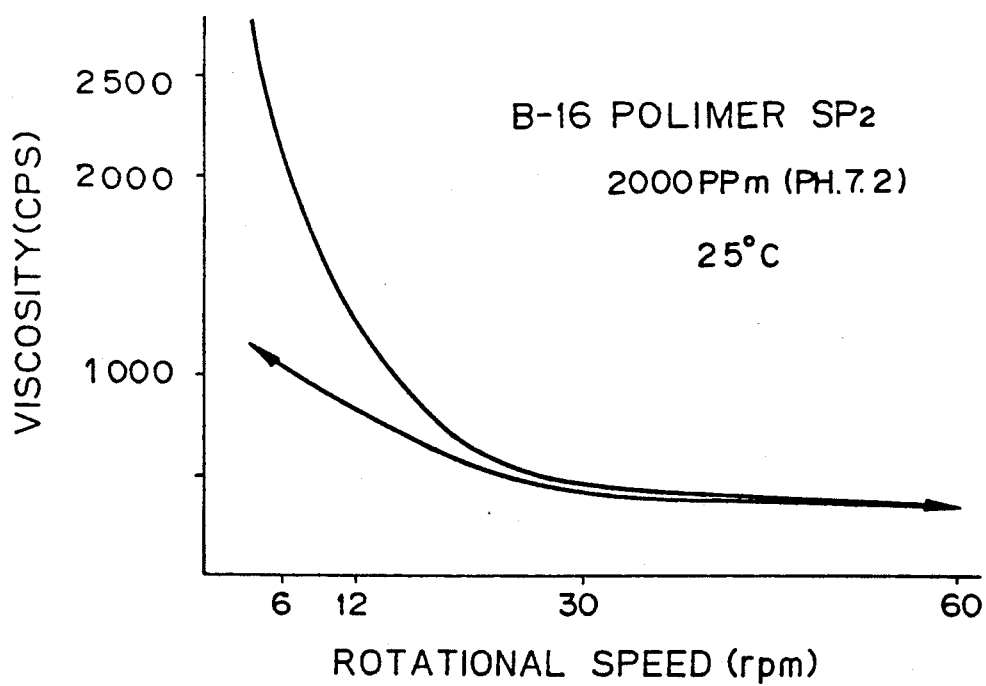

POLYSACCHARIDE, AND WATER ABSORBENT, MOISTURE ABSORBENT OR HUMECTANT AND THICKENING AGENT CHIEFLY MADE OF THE POLYSACCHARIDE

BACKGROUND OF THE INVENTION

1. Field of the Invention

This application is a Continuation-in-Part of U.S. patent application Ser. No. 469,076, filed on Jan. 19, 1990, which was abandoned.

The present invention relates to a polysaccharide (hereinafter referred to as Biopolymer B-16) being produced by cultivating *Alcalioenes latus* strain B-16 (FERM BP-2015), as well as a method of enhancing their production.

On Aug. 24, 1988, *Alcaligenes latus* strain B-16 was deposited with the Fermentation Research Institute, the Agency of Industrial Science and Technology under the accession number FERM BP-2015 as a Budapest Treaty Deposit. The present invention is expected to find use in a broad range of applications including water absorbents, moisture absorbents, humectants, thickening agents, suspension stabilizers, emulsion stabilizers and dispersants such as sanitary articles and paper diapers, cosmetics and even covering humectants for water irrigation of seedlings to be used in the greening of deserts.

2. Description of the Prior Art

With the recent modernization of life style, the consumption of sanitary articles and paper diapers is increasing year by year. Most of the water absorbents, moisture absorbents and paper diapers are based on synthetic high polymer materials. Since the currently available sanitary articles and paper diapers are of a disposable type, they are washed in flush toilets and discharged into the environment. However, they are essentially not biodegradable and will remain in the environment for a prolonged period of time. This is not only unseemly but also deleterious to the environment. Thus, the development of alternatives that are biodegradable and which, hence, are compatible with the environment is strongly desired.

With recent advances in biotechnology, attempts have been made to incorporate biomaterials in cosmetics. However, the use of such "biocosmetics" is very limited and there has been a growing need for the development of new organism-derived moisture absorbents or humectants and thickening agents that can be used as the base of cosmetics.

Accelerated expansion of deserts is currently a global concern over the ecology of the earth. Japan is making a contribution to the greening of deserts by supplying Egypt and other desert countries with synthetic high polymer water absorbents, moisture absorbents or humectants that are to be used to retain water for irrigating seedlings. If such water absorbents, moisture absorbents or humectants and thickening agents were organism-derived and have biodegradability properties and compatibility with the environment, they would hardly cause adverse effects on the environment after the growth of the seedlings.

Some biopolymers being relevant to Biopolymer B-16 of the subject invention have been reported: E. P. Application No. 23,397, which discloses a biopolymer produced by a microorganism which comprises in its structure glucose, galactose, mannose, fucose and glucuronic acid; E. P. Application No. 64,354, which discloses a biopolymer which comprises in its molecule rhamnose, glucose, mannose and glucuronic acid; G. B. U.S. Pat. Nos. 2,058,106 and 2,058,107, which disclose a biopolymer produced by a microorganism which comprises the structure rhamnose, glucose, mannose, galactose and glucuronic acid; and U.S. Pat. No. 4,454,316, which discloses a biopolymer which comprises in its molecule rhamnose, glucose, mannose, galactose and glucuronic acid; Japanese Patent Public Disclosure (Laid-Open) No. 53101/1981, which discloses a biopolymer produced by a microorganism which comprises mannose, glucose, galactose and trace amounts of fucose, arabinose and xylose; Japanese Patent Public Disclosure (Laid-Open) No. 147403/1983, which discloses a biopolymer produced by a microorganism which comprises rhamnose, mannose and N-acetyl glucosamine; and Japanese Patent Public Disclosure (Laid-Open) No. 2194/1985, which discloses a biopolymer produced by a microorganism which comprises glucose, mannose, galactose and glucuronic acid. However, none of the aforementioned prior art references disclose Biopolymer B-16, which comprises rhamnose, fucose, glucose, mannose and glucuronic acid according to the subject invention.

SUMMARY OF THE INVENTION

It is an object of the present invention to provide Biopolymer B-16 consisting essentially of rhamnose, fucose, glucose, mannose and glucuronic acid which are present in a molar ratio of (1–10):(2–10): (4–20):(1):-(1–5).

Another object of the present invention is to provide a water absorbent, moisture absorbent, humectant, thickening agent, suspension stabilizer, emulsion stabilizer or dispersant comprising Biopolymer B-16 that overcomes and eliminates the problems with conventional synthetic high polymer versions and which, hence, has high biodegradability and can be used without causing potential environmental hazards such as secondary pollution.

Another purpose of the present invention is to provide a method of producing such improved water absorbent, moisture absorbent or humectant and thickening agent by cultivating a microorganism.

Other objects and advantages of the present invention may become apparent to those skilled in the art from the description and the drawings.

BRIEF DESCRIPTION OF THE DRAWINGS

FIG. 3 is a diagram showing the results of three measurements conducted to determine the intrinsic viscosity ($\eta$=42) of Bipolymer B-16 produced in accordance with the present invention. The vertical axis plots the intrinsic viscosity ($\eta$) and the horizontal axis plots the concentration of sample (ppm);

FIG. 4-A is a liquid chromatographic chart for standard samples (neutral sugars: glucose, mannose, rhamnose and fucose). The vertical axis plots the dielectric constant ($\times 10^{-1}$ volts) and the horizontal axis plots the retention time ($\times 10$ minutes).

FIG. 4-B is a liquid chromatographic chart for the HCl hydrolyzate of Biopolymer B-16 produced in accordance with the present invention. The vertical and horizontal axes plot the same parameters as in FIG. 4-A;

FIG. 4-C is a diagram showing the relationship between the UV absorbance of a standard sample and retention time (minute);

FIG. 4-D is a diagram showing the relationship between the UV absorbance of the hydrolyzate of Biopolymer B-16 produced in accordance with the present invention and the retention time (minute);

FIG. 5-A shows a gas chromatographic pattern of trimethylsilyated derivatives of standard samples [rhamnose, fucose, uronic acid (glucuronic acid), mannose and glucose]. The vertical axis plots the peak height and the horizontal axis plots the retention time (minutes);

FIG. 5-B shows a gas chromatographic pattern of a trimethylsilyated derivative of the hydrolyzate of Biopolymer B-16 produced in accordance with the present invention. The vertical axis plots the peak height and the horizontal axis plots the retention time (minute);

FIGS. 6-1B, 6-2B, 6-3B and 6-4B show the mass spectra for rhamnose, fucose, glucose and mannose, respectively, of a trimethylsilyated derivative of the hydrolyzate of the biopolymer produced in accordance with the present invention. The vertical axis plots the intensity and the horizontal axis plots the m/e;

FIG. 7-A shows a gas chromatographic pattern of trimethylsilylated derivatives of standard sugars at specified concentrations. The vertical axis plots the peak height and the horizontal axis plots the retention time (minutes);

FIG. 7-B shows a gas chromatographic pattern of a trimethylated derivative of the hydrolyzate of SP produced in Example 1. The vertical axis plots the peak height and the horizontal axis plots the retention time (minute);

FIG. 9 is a graph showing the viscosity vs concentration characteristics of a biopolymer of the present invention (SP$_2$) and Kelzan (control), with the vertical and horizontal axes plotting the viscosity (cps) and the polymer concentration (w/w %), respectively;

FIGS. 10-A and 10-B show fluidity curves for aqueous solutions of SP$_2$ and Kelzan, with the vertical and horizontal axes plotting viscosity (cps) and the rotational speed of spindle (rpm), respectively;

DETAILED DESCRIPTION OF THE PREFERRED EMBODIMENT

Figure 1:
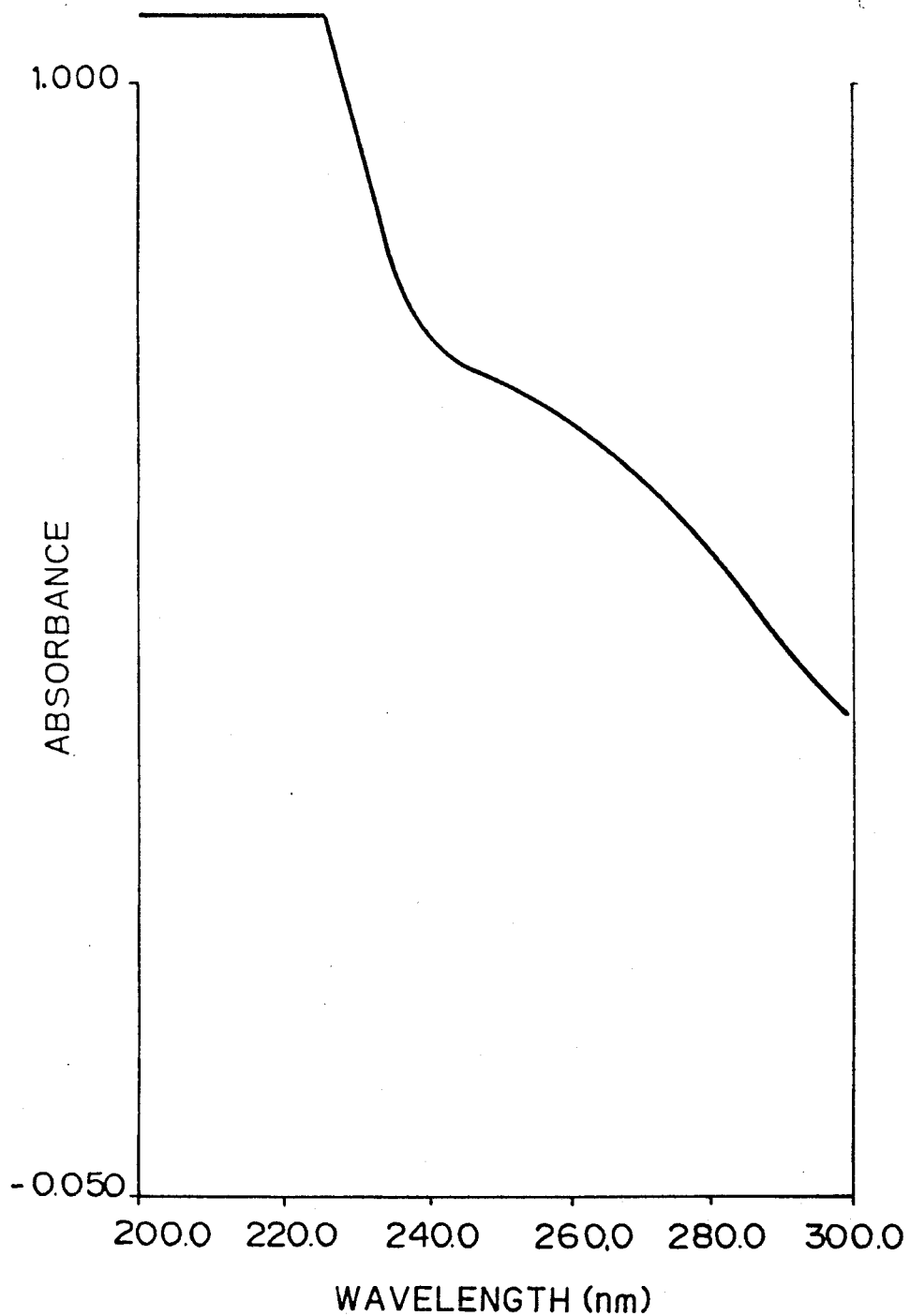
FIG. 1 is a UV absorption spectrum of Biopolymer B-16, produced in accordance with the present invention. The vertical axis plots light absorbance and the horizontal axis plots wavelength (200–300 nm)

The only organism that can be used in the present invention is *Alcaligenes latus* strain B-16 which has been deposited with the Fermentation Research Institute, the Agency of Industrial Science and Technology, under accession number FERM BP-2015.

The morphological and biochemical characteristics of this strain are shown in Table 1 below. Comparing these mycological properties with those described on page 372 of Bergey's Manual of Systematic Bacteriology, Volume 1, 1984, the present inventors found that the strain belongs to the genus Alcaligenes and is compatible with the environment. The type strain (ATCC 29712) is different from FERM BP-2015 in terms of the following aspects described in Table 1: deoxyribonuclease, citric acid, alginin dehydrase, acrylamidase, acid formation from sugars and the ability to produce extracellular polymers, but the two strains are identical in all other aspects.

TABLE 1

| Properties | |
|---|---|
| Gram's stain | — |
| Morphology | short rod |
| Motility | + |
| Flagellum | peritrichous |
| Aerobic growth | + |
| Catalase | + |
| Oxidase | (+)* |
| OF test | 0 |
| Deoxyribonuclease | — |
| Nitric acid reduction | — |
| Citric Acid | — |
| Alginin dehydrase | — |
| Acrylamidase | — |
| Acid formulation from sugars | |
| glucose | + |
| maltose | + |
| xylose | + |
| fructose | + |
| sucrose | + |
| mannitol | — |
| Extracellular polymer producing ability | + |
| GC content (%) | 72 ± 1 |

*(+): weakly positive.

A process for production of Biopolymer B-16 comprises the steps of:

(i) preparing an aqueous culture medium comprising a source of carbon, a source of phosphorus, a source of inorganic nitrogen, a source of sodium and magnesium, and further a source of organic nitrogen, the pH of the culture medium being maintained at a value of from 4 to 10 preferably about 7;

(ii) sterilizing the medium at about 121° C., for 15 minutes, and inoculating the medium with Alcaligenes latus strain B-16 to cultivate it under aerobic conditions;

(iii) isolating Biopolymer B-16 from the culture medium as follows.

After 3-6 days of cultivation, a biopolymer was harvested and purified from the culture broth by the following procedure.

The culture (500 ml) was mixed with two volumes of ethanol and the mixture was left to stand. The liquid phase was removed from the mixture and the precipitate was recovered. To the recovered precipitate, 100 ml of pure water was added and the precipitate was dissolved by being heated on a hot water bath at 60°-70° C. To the solution, five volumes of ethanol were added and the precipitate was recovered. By repeating the cycle of dissolution and precipitation several times, coloring materials that would have been derived from the components of the culture medium were eliminated from the system and a white precipitate was obtained.

The preferred carbon sources for the growth of this strain include not only monosaccharides and oligosaccharides such as fructose, glucose and sucrose, but also natural polymers such as hemilcellulose, starch and corn starch, and oils such as olive oil. Other medium constituents that can be used include inorganic nitrogen sources such as urea ammonium chloride, ammonium nitrate and ammonium sulfate; organic nitrogen sources such as tryptone, yeast extract, meat extract, peptone and malt extract; and inorganic salts such as potassium phosphate, magnesium sulfate and sodium salt.

Using monosaccharides or disaccharides as carbon sources is particularly preferred for the purpose of producing a water absorbent, moisture absorbent or humectant. Cultivation with phosphate added at a concentration of at least 80 mM is also desirable for enhanced production of these agents.

The cultivation may be a liquid cultivation. The initial pH for the cultivation ranges from 4 to 10, with the temperature adjusted to lie between 15° to 40° C. Cultivation is usually performed with agitation under aerated condition. The cultivation period which depends on carbon source and other factors will usually range from 1 to 10 days, during which a maximum production phase is set.

The culture as treated is colorless and clear or a pale yellow solid anionic polymer with viscosity of about 1,000-15,000 cps. The viscosity measurement is performed with a rotary viscometer after 100 volumes of water (20° C.) is added and completely absorbed by the treated culture.

By cultivation, a culture having a water absorbing, moisture absorbing or moisture retaining ability is obtained. The liquid culture is mixed with twice the volume of ethanol and the mixture is left to stand overnight at 5° C. The resulting precipitate is collected by passage through No. 2 filter paper, washed three times with 70% ethanol, further washed three times with distilled water on filter paper, and dehydrated by freeze-drying or some other suitable method. In this way, a water absorbent, moisture absorbent or humectant can be recovered as a treated product of the culture. It should, however, be noted that the culture need not be treated by the isolation and purification procedures described above and if desired, it may be immediately put to use.

The water or moisture that can be absorbed or retained by the agent of the present invention is not limited to any particular type. It is generally held that the effectiveness of synthetic high polymer water absorbents, moisture absorbents or humectants is appreciably reduced in salt water compared to their ability in pure water. However, as will be apparent from the examples that are given later in this specification, the organism-produced water absorbent, moisture absorbent or humectant of the present invention exhibits its intended effect even in the presence of salt and this may as well be considered a novel and outstanding feature over the conventional synthetic high polymer versions.

The methods by which the agent of the present invention absorbs water or moisture and retains moisture are in compliance with the standard assay methods described below for evaluating the performance of said agent. It should however be noted that the methods of implementing the present invention are by no means limited to these standard methods alone.

The capabilities of the agent of the present invention for absorbing water, absorbing moisture and retaining moisture were measured by the following methods.

(A) Water Absorbing Capability

A method generally referred to as a "tea bag method" was adopted. A container having a capacity of about 20 ml was made from a non-woven fabric ("Kitchen Tauper" of Tokai Pulp Co., Ltd.; 100% natural pulp) and charged with a predetermined weight of a sample such as a dried polymer. Then, the container was immersed in pure water for 2 hours, recovered and left to stand for 1 hour to remove the surplus water. The dehydrated sample was put into a constant weight beaker (10 ml) and its weight after water absorption (the weight of water absorbed + sample's weight) was measured exactly. Thereafter, the sample was dried at 105° C. for ca. 15 hours to completely evaporate the water. The exact weight of the sample was again measured.

After these measurements, the amount of water absorption (g) per gram of the dried sample was calculated by the following equation:

$$\text{Water absorption} = \frac{\text{sample weight after absorption (g)} - \text{sample weight before absorption (g)}}{\text{dried sample's weight (= sample weight before absorption) (g)}}$$

(B) Moisture Absorbing Capability

Measurements were conducted in accordance with the method described in Koshokaishi (J. of Perfume and Cosmetics), Vol. 8, No. 2, p. 131 (1984) as follows. Desiccators which respectively contained a saturated solution of potassium nitrate (91% r.h.), a standard solution of sodium nitrate (61.8% r.h.) and a saturated solution of magnesium chloride (31.9% r.h.) were used as stored in a thermostatic chamber at 37° C. Dried samples were exactly weighed in an amount of about 100 mg in plastic cups (i.d. 1.2 cm; product of Sanplatec Corp.) and left to stand in the desiccators. After 2, 4, 6, 8 and 24 hours, the weights of the samples were measured and the percentages of moisture absorbed by these samples were determined by the following equation:

$$(\%) = \frac{W_t - W_o}{W_o} \times 100$$

where $W_o$ is the sample weight before standing and $W_t$ is the sample weight measured at given intervals.

(C) Moisture Retaining (Water Holding) Capability

The method of measuring the moisture retaining capability is described in Koshokaishi, ibid. Desiccators which respectively contained a saturated solution of sodium nitrate (64.8% r.h.), a saturated solution of magnesium chloride (33% r.h.) and phosphorus pentoxide (34% r.h.) were used as stored in a thermostatic chamber at 20° C. Additional desiccators which respectively contained a saturated solution of sodium nitrate (64.8% r.h.) and silica gel were also used as stored in a thermostatic chamber at 20° C. Dried samples were exactly weighed in amounts of about 100 mg
in plastic cups, mixed with 20 μl of water, exactly weighed again and left to stand in the desiccators. After the standing, the weights of the respective samples were measured as in (B) and their ability to retain moisture was determined by the following equation, with the percentage of residual water being used as an index:

Percentage of residual water $$(\%) = \left(1 - \frac{W_o - W_t}{20}\right) \times 100$$

where $W_o$ is the weight of the hydrous sample before standing and $W_t$ is the weight of the hydrous sample measured at given intervals.

EXAMPLES

The present invention is hereunder described in greater detail by way of Examples and Comparative Examples which are given here for illustrative purposes only and are by no means intended to limit the scope of the invention.

EXAMPLE 1

Production of Water Absorbent, Moisture Absorbent or Humectant by Cultivation and Recovery of the Same Sucrose (15 g), $KH_2PO_4$ (6.8 g), $K_2HPO_4$ (8.8 g), $MgSO_4.7H_2O$ (0.2 g), NaCl (0.1 g), urea (0.5 g) and meat extract (0.5 g) were dissolved in 1,000 ml of distilled water and the medium was adjusted to a pH of 7.4. A portion (150 ml) of the medium was transferred into a 500-ml conical flask and sterilized by autoclaving at 120° C. for 15 minutes. Thereafter, a loopful of the *Alcalioenes latus* strain B-16 (FERM BP-2015) was inoculated into the medium in the flask and subjected to rotary shaking culture at 30° C. (180 rpm).

After 6 days of cultivation, a biopolymer was harvested and purified from the culture broth by the following procedure.

The culture (500 ml) was mixed with two volumes of ethanol and the mixture was left to stand. The liquid phase was removed from the mixture and the precipitate was recovered. To the recovered precipitate, 100 ml of pure water was added and the precipitate was dissolved by being heated in a hot water bath at 60°–70° C. To the solution, five volumes of ethanol were added and the precipitate was recovered. By repeating the cycle of dissolution and precipitation several times, coloring materials that would have been derived from the system and a white precipitate was obtained. The white precipitate obtained by the decoloring step described above was diluted and redissolved in 4000–8000 ml of a 0.02% NaOH solution, heated at 121° C. for 10 minutes and subjected to dilution and centrifugation at 40,000 g×40 minutes in order to remove the cells. The cell-free supernatant was neutralized with hydrochloric acid and concentrated with a rotary evaporator at 60°–70° C. To the concentrate, 100 ml of pure water was added and the concentrate was redissolved by heating in a hot water bath at 60°–70° C. To the solution, five volumes of ethanol was added and a precipitate was obtained. After repeating the cycle of dissolution and precipitation with ethanol three times, the precipitate was vacuum-dried at ordinary temperatures to obtain a white purified biopolymer.

By the purifying step described above, 2.4–3 g of a white purified biopolymer was obtained from 1,000 ml of the culture.

The purified biopolymer obtained in Example 1 had the following physicochemical properties.

(1) Color: white
(2) Carbonization temperature: 225°–280° C.
(3) Elemental analysis:

Carbon and hydrogen contents were determined with a Carlo Erba C & H Analyzer (Carlo Erba S.P.A.). The oxygen content was calculated by subtracting the sum of C and H contents from 100 (wt%):

| | |
|---|---|
| C | 40 ± 4 |
| H | 6 ± 1 |
| O | 54 ± 5 |

(4) Solubility:
Slightly soluble in water (neutral); soluble in alkalies; insoluble in methanol, ethanol and acetone; (5) UV absorption spectrum:

As shown in FIG. 1, no absorption was detected at 280 nm characteristic of proteins (peptides) and at 260 nm characteristics of nucleic acids.

Figure 2:
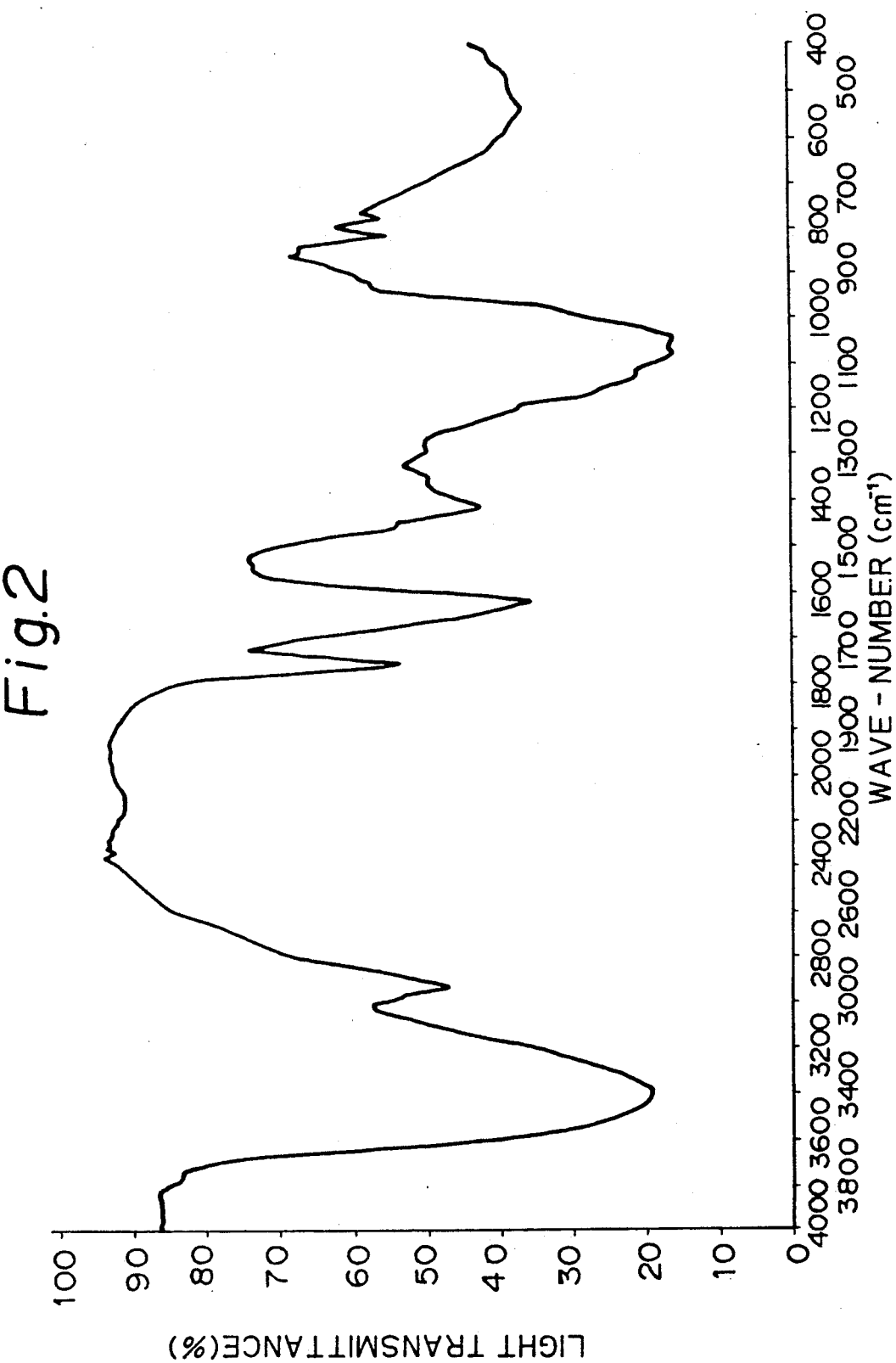
FIG. 2 is an IR absorption spectrum of Biopolymer B-16 produced in accordance with the present invention. The vertical axis plots light transmittance (%) and the horizontal axis plots wave number (cm$^{-1}$)

(6) IR absorption spectrum:
As shown in FIG. 2, an absorption pattern characteristic of polysaccharides was observed near 800–1200 $cm^{-1}$; an absorption pattern characteristic of uronic acid was observed at 1620±20 $cm^{-1}$; CH and $CH_2$ absorption patterns due to carbohydrates were observed near 2950 $cm^{-1}$; and an OH absorption pattern due to carbohydrates was observed near 3400±20 $cm^{-1}$.

(7) Viscosity:
The viscosity of the biopolymer was measured with a Ubbelohde's viscometer with 0.2 N $NaNO_3$ being used as a solvent. The results of measurement are shown in FIG. 3. This biopolymer was found to have an intrinsic viscosity (η) of 42.

(8) Optical rotation:
The biopolymer of interest (100 ppm) was dissolved in a 0.02% NaOH solution and the solution was filtered through a 0.45 μm Millipore filter. The optical rotation of the filtrate was measured with a polarimeter (Model DIP 360 of Japan Spectroscopic Co., Ltd. with 100 mm of a standard cell). The biopolymer was found to have an optical rotation (α) of 0.002 deg.

(9) Qualitative and quantitative reactions on sugars:
Cultivation was performed as in Example 1 using sucrose or fructose as a carbon source. The cultures were purified and the purified samples obtained were designated SP and FT, respectively. Each sample was subjected to qualitative and quantitative reactions on sugars. In the anthrone reaction and the phenol sulfate procedure, the results were evaluated in terms of glucose. In the Elson-Morgan method, hexosamines (e.g., glucosamine and galactosamine) were used as indicators; in the periodic acid-resorcinol reaction, sialic acids (e.g., N-acetylneuraminic acid and N-glycolylneuraminic acid) were used as indicators; in the carbazole sulfate reaction, uronic acids (e.g., glucuronic acid and galacturonic acid) were used as indicators; and in the orthocin $Fe^{3+}$ method, glucuronic acid was used as an index. The biopolymers of interest were hydrolyzed by the following scheme. The results of reactions performed on the respective samples are summarized in Table 2.

Method of Hydrolyzing Polysaccharides heat in 2 N H₂SO₄ at 100° C. for 2 hours (sealed under vacuum)

↓ neutralize with BA(OH)₂

↓ centrifuge at 18,000 rpm for 5 minutes to remove the precipitate

↓ stir with activated carbon for 5 minutes

↓ centrifuge at 19,000 rpm for 5 minutes to remove the precipitate

↓ filter through 0.45-μm membrane

↓ concentrate with evaporator at 50° C.

TABLE 2

Qualitative and Quantitative Reactions on Constituent Sugars

| Reaction | Sugar content in each sample | |
|---|---|---|
| | SP | FP |
| Anthrone reaction | 76% | 66% |
| Phenol sulfate procedure | 78% | 58% |
| Elson-Morgan | — | — |
| Periodic acid-resorcinol reaction | — | — |
| Carbazole sulfate reaction | 19% | 17% |

In the anthrone reaction and the phenol sulfate procedure, the results were expressed in percentages in terms of glucose.

The results of the qualitative and quantitative reactions on sugars suggest the possibility that the biopolymers of interest have hexose and uronic acids as constituents. It is however clear that the biopolymers do not have hexamines such as glucosamine or sialic acids such as N-acetylneuraminic acid.

(10) Constituent sugars:

Now that it was established that the biopolymers of interest had sugars such as hexose and uronic acids, they were hydrolyzed with an acid such as hydrochloric acid and subjected to identification of constituent sugars by thin-layer chromatography, liquid chromatography, gas chromatography and mass spectroscopy.

(A) Thin-Layer Chromatography

Cultivation was performed as in Example 1 using sucrose as a carbon source and the culture was purified to obtain sample SP. A hydrolyzate of this sample was subjected to thin-layer chromatography under various developing conditions including solvent system. Rf values of known sugars and the hydrolyzate of the sample as obtained for various developing solvents are summarized in Table 3-1 (comparison of Rf values between each standard sugar and the hydrolyzate of the sample), Table 3-2 (comparison with mannose) and Table 3-3 (comparison with glucuronic acid as uronic acid).

The following conditions were used to identify constituent sugars by thin-layer chromatographic analysis.

Identification of Sugars by TLC
Experimental conditions:

| 1. TLC plate | α. Kiesel Gel 60 of Merck |
| | β. Silica Gel 60A of Whatman |
| 2. Developing temperature | 50° C. |
| 3. Color producing agent | i) diphenylamine-aniline-phosphate reagent |
| | ii) naphthoresorcinol phosphate reagent |
| | iii) potassium permanganate reagent |
| 4. Developing solvent | a) 1-propanol/water = 85/15 |
| | b) ethyl acetate/acetic acid/methanol/water = 60/15/15/10 |
| | c) t-butanol/acetone/0.1M lactic acid = 4/4/2 |
| | d) isopropanol/acetone/0.1M lactic acid = 4/4/2 |
| | e) acetone/0.1M lactic acid/ethyl acetate = 6/2/2 |
| | f) t-butanol/acetone/0.2M lactic acid = 6/2/2 |
| | g) isopropanol/0.1M lactic acid/methanol - 4/2/4 |
| | h) ethyl acetate/acetic acid/methanol/0.1M lactic acid = 60/10/25/5 |
| 5. Preconditioner of TLC plate | A. 0.1M NaHSO₃ |
| | B. 0.5M NaH₂SO₄ |
| 6. Unless otherwise noted, only one development was done. | |

TABLE 3-1

Rf Values in Thin-Layer Chromatography of Standard Sugars and Hydrolyzates of the Sample

| | SP Rf plate α, color producing reagent i, solvent c, preconditioner B, developed twice | Rf plate β, color producing reagent i, solvent d, preconditioner B, developed once |
|---|---|---|
| Sample | 0.05,0.37,0.45,0.57,0.78, 0.88,0.92,0.95 | 0.40,0.52,0.79,0.94 |
| D-glucose | 0.33 | 0.40 |
| D-galactose | 0.21 | 0.22 |
| D-mannose | 0.43 | 0.49 |
| D-xylose | 0.55 | 0.65 |
| L-arabinose | 0.50 | 0.46 |
| D-ribose | 0.66 | |
| L-ribose | 0.42 | |
| L-fucose | 0.78 | 0.77 |
| L-rhamnose | 0.91 | 0.92 |
| 2DOX-D-glucose | 0.84 | 0.88 |
| 2DOX-D-ribose | 0.94 | |
| D-glucuronic acid | 0.75,0.79,0.83,0.85,0.95 | 0.94 |
| D-galacturonic acid | 0.19 | |
| D-galactosamine | 0.03,0.55,0.70,0.83 | |
| D-trehalose | 0.18 | |
| Maltose | 0.19 | |
| D-lactose | 0.13,0.23 | |
| D-celbiose | 0.21,0.94 | 0.24 |
| Melibiose monohydrate | 0.07 | 0.15 |
| Methyl-α-D-glucopyranoside | 0.87 | |
| Salicin | 1.0 | |
| Raffinose | 0.06 | |
| Gulose | | 0.48 |

TABLE 3-1-continued

Rf Values in Thin-Layer Chromatography of
Standard Sugars and Hydrolyzates of the Sample

| | SP plate α, color producing reagent i, solvent c, preconditioner B, developed twice | Rf plate β, color producing reagent i, solvent d, preconditioner B, developed once |
|---|---|---|
| Allose | | 0.42 |
| Talose | | 0.51 |

TABLE 3-2

Separation and Determination of Hexose (mannose)

| | Rf |
|---|---|
| Experimental conditions: α, ii, g, B | |
| Sample | 0.14, 0.20, 0.37, 0.56 |
| Mannose | 0.19 |
| Talose | 0.22 |
| Talose + sample | 0.16, 0.21, 0.26, 0.40, 0.60 |

TABLE 3-3

Separation and Determination of Uronic Acids

| | Rf |
|---|---|
| (1) Experimental conditions: α, 1, g, B | |
| Sample | 0.23, 0.73, 0.89, 0.94 |
| Galacturonic acid | 0.09 |
| Glucuronic acid | 0.17 |
| Mixture of the above | 0.1, 0.21 |
| (2) Experimental conditions: α, ii, e, A | |
| Sample | 0.11, 0.5, 0.67, 0.77 |
| Muramic acid | 0.16 |
| Mannuronic acid lactone | 0.73 |
| (3) Experimental conditions: α, iii, b, A | |
| Sample | 0.11, 0.26, 0.43, 0.64, 0.83 |
| Glucono lactone | 0.26, 0.51, 0.93 |
| Giulono lactone | 0.07, 0.31, 0.43, 0.57, 0.67 |

TABLE 3-4

Rf Values in Thin-Layer Chromatography of Hydrolyzates
of the Sample and a Mixture of Five Standard Samples
(glucose, mannose, rhamnose, fucose and gucuronic acid)

| Condition | Sample (hydrolyzate) | Mixture (of standard sample) |
|---|---|---|
| α, i, a, A developed twice | 0.11, 0.2, 0.58 0.68, 0.75, 0.82 | 0.14, 0.56, 0.61 0.73, 0.80 |
| α, i, b, A developed twice | 0.36, 0.42, 0.53 0.68, 0.80, 0.85 | 0.24, 0.31, 0.39 0.52, 0.71, 0.81 0.85 |
| α, i, c, B developed twice | 0.33, 0.5, 0.73 0.91, 0.95 | 0.38, 0.5, 0.74, 0.9, 0.95 |
| β, i, d, B | 0.41, 0.54, 0.78 0.95, 0.98 | 0.40, 0.52, 0.77 0.94, 0.98 |

The data in Table 3-1 shows that the biopolymer of interest contains glucose, rhamnose and fucose since it has Rf values in agreement with those of glucose, rhamnose and fucose, as standard.

As shown in Table 3-2, talose had an Rf value similar to that of mannose. Thus, talose was compared with the hydrolyzate of the sample under various conditions. As a result, it was found that the sample biopolymer contained mannose rather than talose as a constituent sugar.

In order to make further sure that glucuronic acid was a constituent uronic acid, an experiment was conducted under the three conditions shown in Table 3-3. As shown under Experimental Conditions (1), glucuronic acid alone had an Rf value of 0.17, but in the presence of galacturonic acid, even the standard sample had a higher Rf value of 0.21. The experiment conducted under the other conditions showed that the uronic acid was neither muramic acid nor mannuronic acid lactone. It therefore became apparent that the biopolymer of interest contained glucuronic acid as a uronic acid.

With these results taken into consideration, five standard samples (glucose, mannose, rhamnose, fucose and glucuronic acid) in the admixture and the hydrolyzate of the biopolymer of interest were subjected to thin-layer chromatography under four conditions (see Table 3-4). As shown in Table 3-4, the five standard samples had Rf values which were in very good agreement with those of the hydrolyzate of the biopolymer.

Thus, the results of detailed analyses by thin-layer chromatography showed that the biopolymer of interest contained five sugars, glucose, mannose, rhamnose, fucose and glucuronic acid, as constituents.

(B) High-Performance Liquid Chromatography

The neutral sugars (rhamnose, fucose, mannose and glucose) identified by thin-layer chromatography were analyzed with a high-performance liquid chromatography using Amide-80 (Tosoh Corp.) as a column: mobile phase, acetonitrile/water =80/20; flow rate, 1.0 ml/min.; column temperature, 80° C.; detector, RI. Liquid chromatographic charts for the standard samples of the neutral sugars and the hydrolyzate of the biopolymer sample prepared in Example 1 are shown in FIG. 4-A and FIG. 4-B, respectively. As shown in these figures, the hydrolyzate of the biopolymer sample of interest had peaks 1, 2, 3 and 4 which respectively corresponded to rhamnose, fucose, mannose and glucose.

A standard sample of glucuronic acid and the hydrolyzate of the biopolymer were compared by high-performance liquid chromatography using a phenol-form column (Waters, Inc.): mobile phase, methanol/water =80/20; flow rate, 0.5 ml/min.; detector, UV. The results are shown in FIG. 4-C and FIG. 4-D, from which one can see that the two samples had the same retention time.

The above results show that the biopolymer of interest as analyzed by high-performance liquid chromatography (HPLC) contained glucose, mannose, rhamnose, fucose, and glucuronic acid as constituent sugars.

(C) Gas Chromatography and Gas Mass Spectroscopy

In order to perform a triple check of the constituent sugars identified by TLC and HPLC, the biopolymer of interest was subjected to gas chromatography and gas mass spectroscopy (GC-MS). Simultaneous analysis of neutral sugars and uronic acid (glucuronic acid) was performed by the following procedure: the sample obtained in Example 1 was hydrolyzed with HCl, silylated with a silylating agent, loaded into a gas chromatographic column (supported by Silicone OV-1), heated to a temperature in the range of 50°–200° C., and analyzed by FID. Hydrolysis of the sample was conducted in accordance with the method of hydrolyzing polysaccharides as described on page 13. The hydrolyzate was derivated to a trimethylsilyl form by the following scheme.

Derivation to Trimethylsilyl

Hydrolyzate

-continued
Derivation to Trimethylsilyl

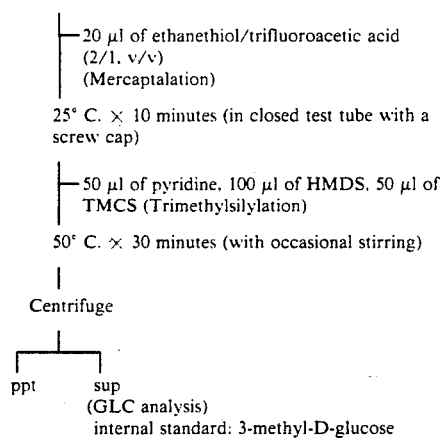

A gas chromatographic pattern of the authentic samples of trimethylsilylated derivatives of glucose, mannose, rhamnose, fucose and uronic acid (glucuronic acid) is shown in FIG. 5-A. A gas chromatographic pattern of the hydrolyzate of the purified biopolymer obtained in Example 1 is shown in FIG. 5-B. As these figures show, the silylated derivative of the hydrolyzate of the sample of interest was in complete agreement with the silylated derivatives of glucose, mannose, rhamnose, fucose and glycuronic acid.

Four peaks that were comparatively large in the gas chromatographic analysis (peak 1, rhamnose; peak 2, fucose; peak 5, glucose; peak 6, mannose) were introduced into a mass spectrograph and subjected to GC-MS analysis.

Figures 1A, 6:
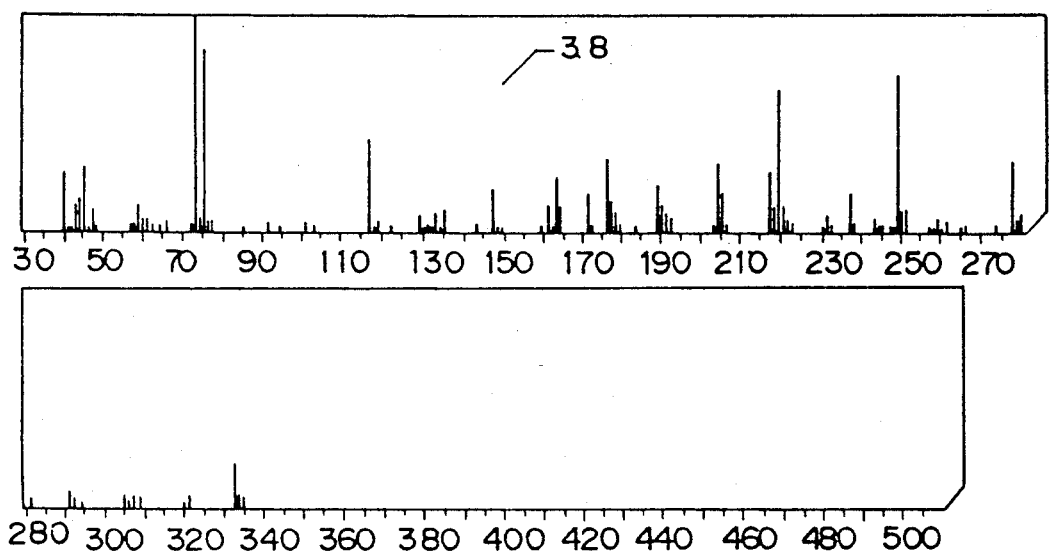
FIGS. 6-1A, 6-2A, 6-3A and 6-4A shows mass spectra for rhamnose, fucose, glucose and mannose, respectively, of trimethylsilyated derivatives of their standard samples. The vertical axis plots the intensity and the horizontal axis plots the m/e.
Figures 1B, 6:
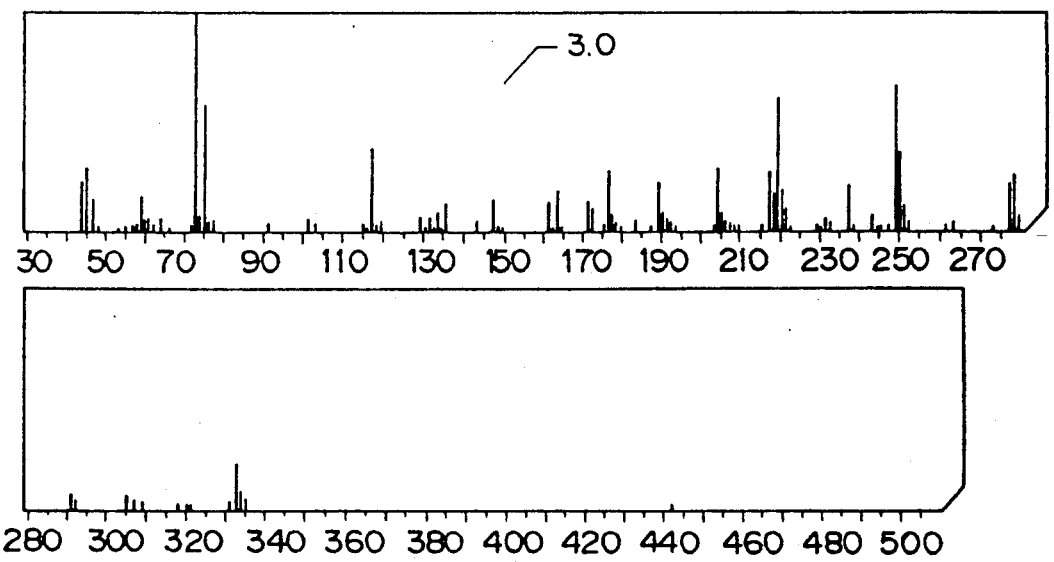
Figures 2A, 6:
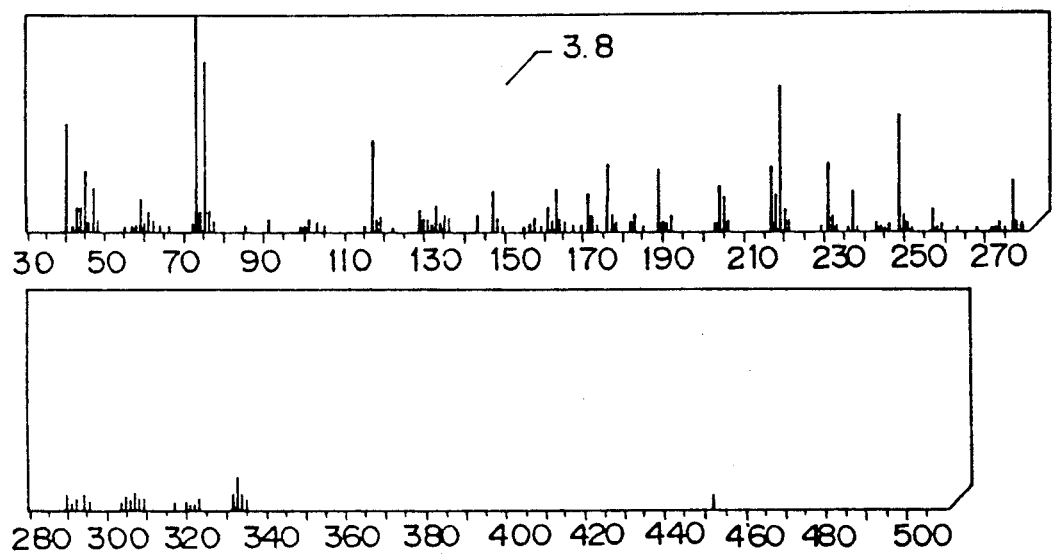
Figures 2B, 6:
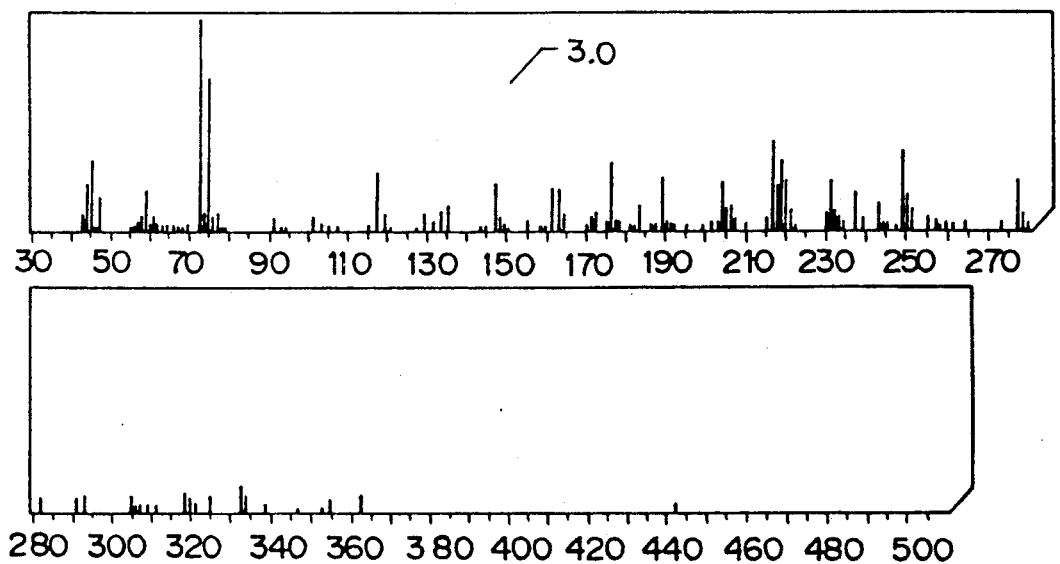
Figures 3A, 6:
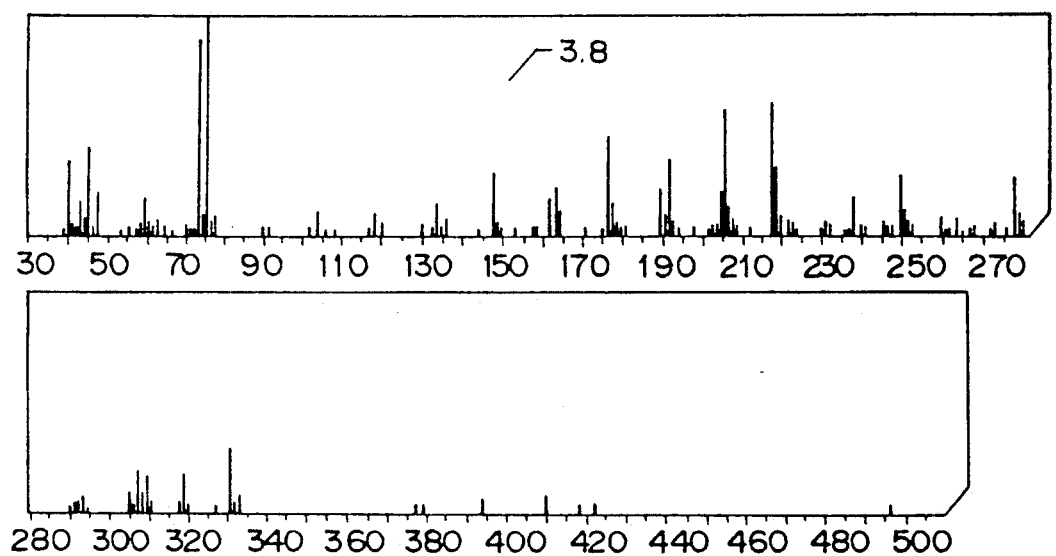
Figures 3B, 6:
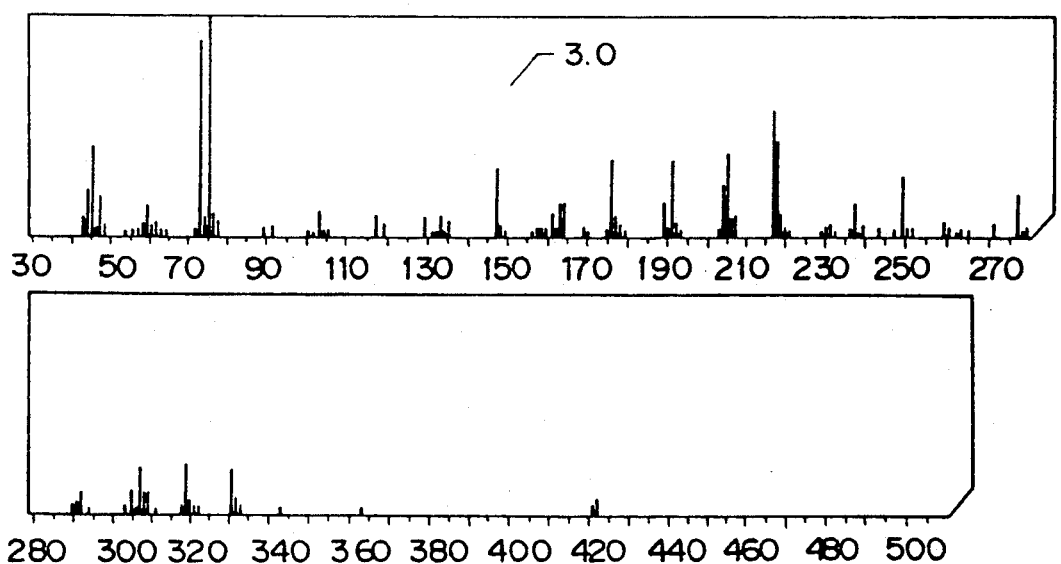
Figures 4A, 6:
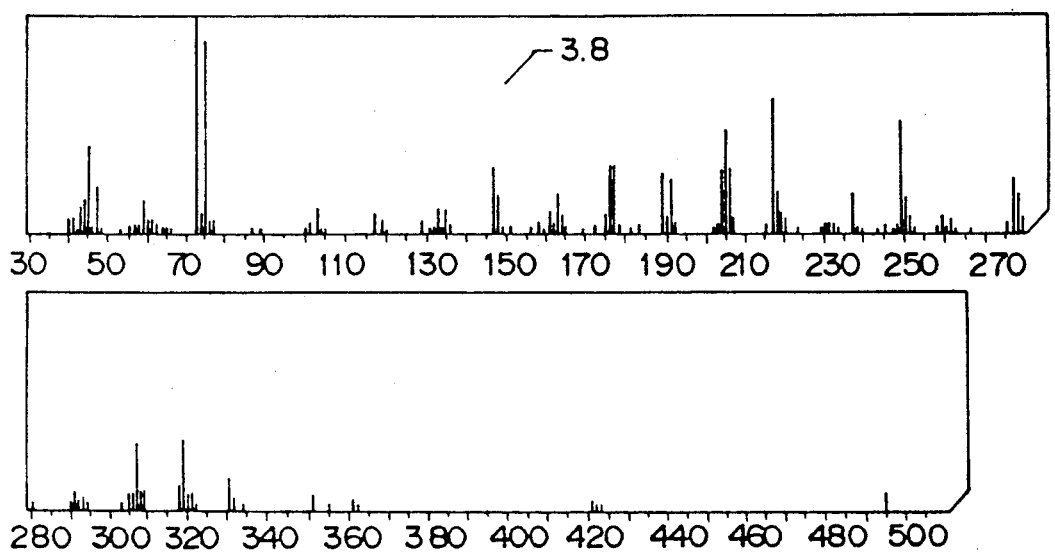
Figures 4B, 6:
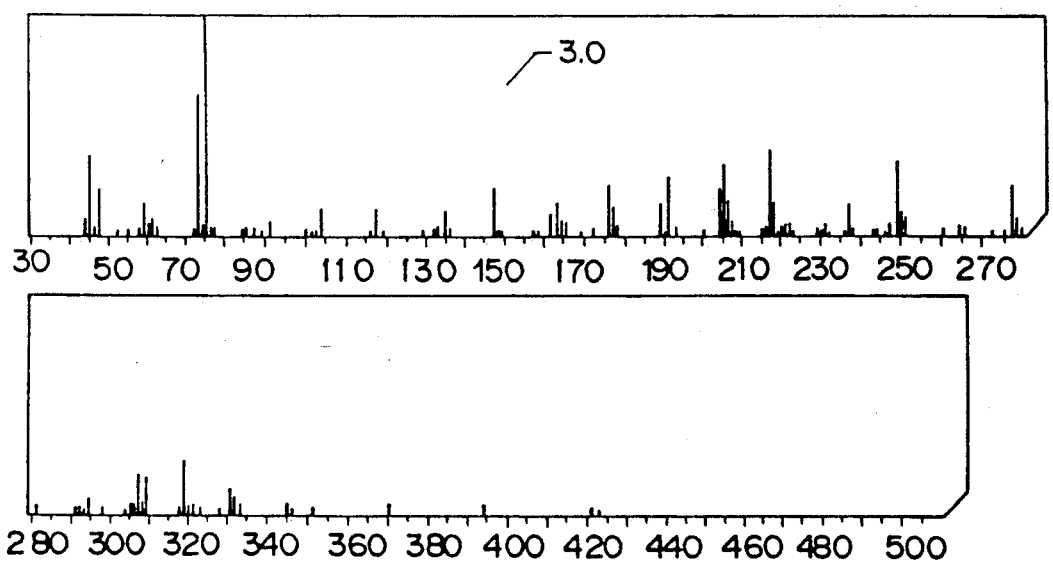

FIG. 6-1A and FIG. 6-1B show the mass spectra of peak 1 and rhamnose for the standard samples and the hydrolyzate of the biopolymer, respectively; FIG. 6-2A and FIG. 6-2B show the mass spectra of peak 2 and fucose for the standard samples and the hydrolyzate, respectively; FIG. 6-3A and FIG. 6-3B show the mass spectra of peak 5 and glucose for the standard samples and the hydrolyzate, respectively; and FIGS. 6-4A and FIGS. 6-4B show the mass spectra of peak 6 and mannose for the standard samples and the hydrolyzate, respectively. As these mass spectra show, the fragments of peaks 1, 2, 5 and 6 are in agreement with those of the standard samples.

Thus, the results of GC-MS analysis also confirm that the hydrolyzate of the biopolymer of interest contained rhamnose, fucose, mannose and glucose as constituent sugars.

In summary, the results of gas chromatography (GC) and gas mass spectroscopy (GC-MS) showed that the hydrolyzate of the biopolymer of interest contained glucose, mannose, rhamnose, fucose and glucuronic acid as constituent sugars.

(11) Molar ratio of constituent sugars:

The molar ratio of the five constituent sugars, rhamnose, fucose, mannose, glucose and glucuronic acid, was determined from the ratio of areas of individual peaks in gas chromatography. The conditions of gas chromatography were the same as those described on pages 21-22. In order to determine the molar ratio of the constituent sugars, the standard samples of specified concentrations were first subjected to gas chromatography and the areas of peaks obtained were determined. Then, the hydrolyzate of the purified biopolymer obtained in Example 1 (for the conditions of hydrolysis, see page 15) was subjected to gas chromatography and the areas of peaks obtained were determined. On the basis of the thus determined peak area, the molar ratio of the constituent sugars under consideration was calculated by the following equation:

$$\text{Molar ratio of constituent sugar} = \frac{\text{Peak area of hydrolyzate (constituent sugar)}}{\text{Peak area of standard sample}} \times (\text{Number of moles of standard sample})$$

The gas chromatographic pattern of the standard samples used is shown in FIG. 7-A, and that of the hydrolyzate of SP (purified biopolymer obtained by cultivation in Example 1 with sucrose used as a carbon source) is shown in FIG. 7-B. The peak area and the number of moles of the standard samples and the hydrolyzate are shown in Table 4 below.

TABLE 4

|  | Standard sample | | SP hydrolyzate | |
|---|---|---|---|---|
|  | Peak area | Number of moles (mmol) | Peak area | Number of moles (mmol) |
| Rhamnose (peak 1) | 14884 | 2.44 | 5196 | 0.853 |
| Fucose (peak 2) | 11037 | 3.05 | 5675 | 1.568 |
| Glucose (peak 5) | 15574 | 2.78 | 17378 | 3.102 |
| Mannose (peak 6) | 13243 | 2.78 | 2730 | 0.573 |
| Glucuronic acid peaks 3 + 4) | 9931 | 4.12 | 3218 | 1.421 |

The molar ratio of the constituent sugars may be calculated as follows with mannose taken as unity:

Rhamnose:fucose:glucose:mannose:glucuronic acid $\approx (1-2):(3-4):(5-6):(1):(2-3)$.

EXAMPLE 2

Effects of Variations in the Type and Concentration of Carbon Sources and the Concentration of Phosphates on the Efficiency of Production of Water Absorbent, Moisture Absorbent or Humectant and Thickening Agent A water absorbent, moisture absorbent or humectant and thickening agent was produced under different culture conditions by changing the type and concentration of carbon sources and the concentration of phosphates as shown in Table 5. The other conditions were the same as in Example 1.

TABLE 5

| Symbol for culture conditions | Carbon source | | Phosphate | |
|---|---|---|---|---|
|  | type | amount (g) | $K_2HPO_4$ (g) | $KH_2PO_4$ (g) |
| SP$_1$ | sucrose | 15 | 8.4 | 4.4 |
| SP$_2$ | sucrose | 15 | 16.8 | 8.8 |
| FP$_1$ | fructose | 15 | 8.4 | 4.4 |
| FP$_2$ | fructose | 15 | 16.8 | 8.8 |
| 1/5 SP$_1$ | sucrose | 3 | 1.7 | 0.9 |
| 1/5 SP$_2$ | sucrose | 3 | 33.6 | 1.8 |
| 1/5 FP$_1$ | fructose | 3 | 1.7 | 0.9 |
| 1/5 FP$_2$ | fructose | 3 | 33.6 | 1.8 |

EXAMPLE 3

Water Absorbing Ability

The water absorbing ability of the samples obtained in Example 2 was measured by the method described in (A). The results are shown in Table 7. The six controls or comparative samples described in Table 6 below were also tested.

TABLE 6

| Comparative sample | Manufacturer | Remarks |
|---|---|---|
| (1) Pulp | | |
| (2) Silica gel | Kanto Chemicals Co., Ltd. | reagent |
| (3) Ion-exchange resin | Dow Chemical | |
| (4) High-grade water-absorbing polymer | Sumitomo Chemical | Sumika Gel S-50 |
| (5) PVA | Unitika Kasei | UP-100G, 8-10 cps, partially saponified |
| (6) Anionic polymer | Sumitomo Chemical | Sumifloc FA-70 (acrylamide/acrylic acid copolymer; MW, $7 \times 10^6$) |

It is obvious from Table 7 that the substances produced by *Alcaligenes latus* absorbed more water at a faster rate than any of the samples in the control group.

TABLE 7

Water Absorption by Biopolymers

| | Sample | Water absorption (g) per gram of dried sample |
|---|---|---|
| Test group | $SP_1$ | 759.6 |
| | $SP_2$* | 593.3 |
| | $FP_1$ | 451.6 |
| | $FP_2$ | 759.6 |
| | 1/5 $SP_1$ | 1349.0 |
| | 1/5 $SP_2$ | 836.8 |
| | 1/5 $FP_1$ | 1295.4 |
| | 1/5 $FP_2$ | 944.5 |
| Control group | Pulp | 3.8 |
| | Silica gel | 1.4 |
| | Ion-exchange resin | 2.5 |
| | High-grade water-absorbing polymer | 249.4 |
| | PVA | 4.6 |
| | Anionic polymer | 363.6 |

EXAMPLE 4

Moisture Absorbing Ability

The moisture absorbing ability of sample $SP_2$ prepared in Example 1 and a new sample MIX which was prepared by mixing all the samples prepared in Example 2 was measured by the method described in (B). The controls compared with $SP_2$ and MIX were the following common moisture absorbents: silica gel; PVP (polyvinylpyrrolidone sold from Wako Chemicals Industries, Ltd. under the trade name K-30); urea (guaranteed reagent available from Kanto Chemicals Co., Ltd.); glycerin (guaranteed reagent available from Kanto Chemicals Co., Ltd.); PEG 200 (Nippon Yushi); and anionic polymer (Sumifloc FA-70 of Sumitomo Chemical). The test results are shown in Table 8 below.

TABLE 8

| Relative humidity | Sample | Moisture absorption (%) at given intervals (h) | | | | | | |
|---|---|---|---|---|---|---|---|---|
| | | 2 | 4 | 6 | 8 | 10 | 24 | 48 |
| 91% | $SP_2$ | 42 | 53 | 61 | 65 | 69 | 93 | 105 |
| | MIX | 38 | 50 | 58 | 62 | 66 | 87 | 99 |
| | silica gel | 31 | 32 | 32 | 32 | 32 | 31 | 31 |
| | PVP | 29 | 34 | 36 | 37 | 39 | 46 | 48 |
| | Urea | 12 | 23 | 35 | 45 | 57 | 114 | 154 |
| | PVA | 8 | 11 | 13 | 13 | 14 | 15 | 16 |
| | glycerin | 33 | 49 | 61 | 68 | 76 | 113 | 140 |
| | PEG 200 | 27 | 38 | 45 | 50 | 55 | 78 | 92 |
| | anionic polymer | 17 | 28 | 35 | 41 | 46 | 64 | 75 |
| | hyaluronic acid | | | | | | 35 | |
| 61.8% | $SP_2$ | 31 | 33 | 34 | 33 | 34 | 33 | 35 |
| | MIX | 28 | 30 | 31 | 32 | 32 | 31 | 30 |
| | silica gel | 28 | 29 | 29 | 29 | 29 | 29 | 29 |
| | PVP | 18 | 19 | 19 | 19 | 19 | 18 | 19 |
| | Urea | 0 | 0 | 0 | 0 | 0 | 0 | 0 |
| | PVA | 3 | 3 | 4 | 5 | 5 | 7 | 7 |
| | glycerin | 23 | 30 | 33 | 35 | 36 | 37 | 38 |
| | PEG 200 | 18 | 20 | 20 | 20 | 20 | 20 | 22 |
| | anionic polymer | 9 | 13 | 16 | 21 | 21 | 22 | 21 |
| | hyaluronic acid | | | | | | 17 | |
| 31.9% | $SP_2$ | 7 | 9 | 6 | 11 | 12 | 12 | 11 |
| | MIX | 9 | 10 | 7 | 14 | 14 | 14 | 14 |
| | silica gel | 13 | 16 | 12 | 18 | 18 | 17 | 16 |
| | PVP | 8 | 9 | 9 | 9 | 9 | 9 | 10 |
| | Urea | 0 | 0 | 0 | 0 | 0 | 0 | 0 |
| | PVA | 0 | 1 | 1 | 1 | 2 | 2 | 2 |
| | glycerin | 6 | 9 | 11 | 12 | 13 | 12 | 12 |
| | PEG 200 | 3 | 7 | 7 | 7 | 7 | 6 | 7 |
| | anionic polymer | 1 | 1 | 1 | 2 | 1 | 3 | 4 |

The data for glycerin and urea were substantially equal to the 24-hour values obtained by the method of (B) described in T. Ando et al., Koshokaisha, ibid, pp 130-134. Tyaluronic acid has recently come to be used in cosmetics as naturally occurring moisture absorbent or humectant and as compared to its 24-hour values described in Ando et al. (ca. 35% at 91% r.h. and 37° C. and ca. 17% at 61.8% r.h. and 37° C.), MIX was from 2.7 to about 2.0 times more effective in absorbing moisture.

Thus it is clear that $SP_2$ and MIX are organism-derived biopolymers that exhibit high moisture absorbing ability.

EXAMPLE 5

Moisture Retaining (Water Holding) Ability

The $SP_2$ and MIX tested in Example 4 were also evaluated for their ability to retain moisture by the method described in (C). The controls were the same as those selected in Example 4. The test results are shown in Table 9.

According to Ando et al., ibid, p. 133, the 24-hour moisture retaining ability of hyaluronic acid (105%) was lower than the values for SPz and MIX, both of which were at least 1.5 times as effective as hyaluronic acid.

By comparing the data in Table 9 with documented values, one will readily see that SPz and MIX, which are organism-derived biopolymers, exhibit high moisture retaining ability.

TABLE 9

| Relative humidity | Sample | Moisture absorption (%) at given intervals (h) | | | | | | |
|---|---|---|---|---|---|---|---|---|
| | | 2 | 4 | 6 | 8 | 10 | 24 | 48 |
| 64.8% | $SP_2$ | 155 | 159 | 162 | 163 | 168 | 167 | 162 |
| | MIX | 160 | 161 | 164 | 167 | 172 | 171 | 167 |
| | silica gel | 133 | 134 | 133 | 133 | 134 | 132 | 131 |
| | PVP | 132 | 118 | 118 | 117 | 120 | 120 | 115 |

TABLE 9-continued

| Relative humidity | Sample | Moisture absorption (%) at given intervals (h) | | | | | | |
|---|---|---|---|---|---|---|---|---|
| | | 2 | 4 | 6 | 8 | 10 | 24 | 48 |
| | Urea | 6 | 3 | 2 | 2 | 1 | 0 | 2 |
| | PVA | 61 | 32 | 30 | 30 | 31 | 31 | 33 |
| | glycerin | 156 | 178 | 189 | 195 | 203 | 207 | 200 |
| | PEG 200 | 140 | 141 | 144 | 146 | 150 | 151 | 143 |
| | anionic polymer | 96 | 99 | 103 | 105 | 111 | 111 | 105 |
| | hyaluronic acid | | | | | | 105 | |
| 33% | $SP_2$ | 100 | 99 | 96 | 95 | 97 | 84 | 82 |
| | MIX | 97 | 94 | 89 | 88 | 90 | 76 | 74 |
| | silica gel | 93 | 94 | 91 | 93 | 94 | 87 | 84 |
| | PVP | 77 | 73 | 70 | 69 | 70 | 63 | 60 |
| | Urea | 5 | 2 | 3 | 3 | 5 | 4 | 6 |
| | PVA | 30 | 27 | 25 | 25 | 25 | 22 | 21 |
| | glycerin | 79 | 76 | 72 | 72 | 74 | 58 | 55 |
| | PEG 200 | 66 | 61 | 57 | 56 | 58 | 46 | 43 |
| | anionic polymer | 43 | 37 | 36 | 35 | 36 | 33 | 33 |
| 34% | $SP_2$ | 51 | 32 | 24 | 26 | 24 | 26 | 9 |
| (measured) | MIX | 56 | 40 | 36 | 34 | 34 | 26 | 17 |
| under | silica gel | 53 | 35 | 28 | 25 | 30 | 29 | 9 |
| $P_2O_{25}$ | PVP | 38 | 24 | 26 | 23 | 20 | 11 | 6 |
| | Urea | −2 | −2 | −2 | −2 | −2 | −2 | −4 |
| | PVA | 37 | 25 | 22 | 20 | 19 | 14 | 9 |
| | glycerin | 39 | 24 | 20 | 18 | 16 | 4 | −2 |
| | PEG 200 | 23 | 12 | 15 | 19 | 11 | 14 | −31 |
| | anionic polymer | 30 | 25 | 22 | 21 | 20 | 16 | 10 |

EXAMPLE 6

Water Absorption Test in the Presence of Salt

It is generally held that the water absorption by synthetic high polymer water absorbents reduces markedly in the presence of salt. Thus, a test was conducted in order to see what would happen to the organism-produced water absorbent, moisture absorbent or humectant of the present invention when it was used in the presence of salt. The sample used in this test was SPz prepared in Example 1. Sodium chloride was added as a salt in an amount of 0.9%. Before being used in the test, the sample was pulverized, frozen and further dried. To insure that the powder would absorb a maximum amount of water, the absorption time was extended from the normal 2 hours to 24 hours.

The control was a commercial, high-grade water-absorbing synthetic polymer (Sumika Gel S-50), which was tested under the same conditions as described above. The test results are shown in Table 10 below.

TABLE 10

| Sample | Water absorbed | Water absorption (g) per gram of dried sample |
|---|---|---|
| $SP_2$ | pure water | 636 (24 hours) |
| | 0.9% physiological saline | 384 (24 hours) |
| control (synthetic high polymer absorbent) | pure water | 200.9 (24 hours) |
| | 0.9% physiological saline | 23.8 (24 hours) |

As Table 7 shows, the water absorbing ability of $SP_2$ certainly reduced in the presence of salt but the decrease was much smaller than what occurred in the control. Although the difference in absorption time precludes a definite conclusion, one may as well say that the water absorption by $SP_2$ in the presence of 0.9% NaCl is comparable to the 2-hour values for Sumika Gel S-50 and Sumifloc FA-70 in pure water which are shown in Table 7 (Example 3).

Thus, it is clear that SPz works satisfactorily as a water absorbent even if it is used in salt water.

EXAMPLE 7

Figure 8:
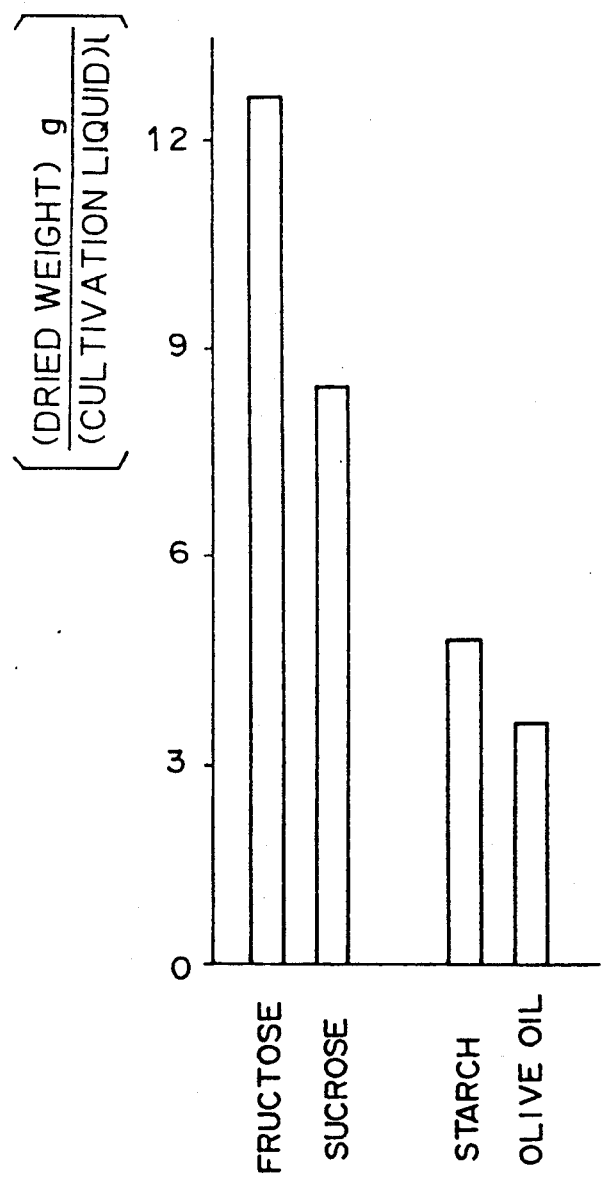
FIG. 8 is a diagram showing the yield of production of a water absorbent, moisture absorbent or humectant and thickening agent when various carbon sources were used in the cultivation of Alcaliœnes latus strain B-16.

Production of Water Absorbent, Moisture Absorbent or Humectant and Thickening Agent in the Presence of Various Carbon Sources Cultivation was performed as in Example 1 except that the following four carbon sources were individually used at a concentration of 15 g/l: fructose as a representative monosaccharide; sucrose as a representative disaccharide; starch as a representative natural polymer; and olive oil as a representative nonaqueous carbon source. A water absorbent, moisture absorbent or humectant and thickening agent was removed from the respective 6-day cultures and its weight on a dry basis was measured to compare the yields of the respective products. The results are shown in FIG. 8, from which one can see that the yield of the desired water absorbent, moisture absorbent or humectant and thickening agent could be increased by selective use of a monosaccharide or disaccharide as a carbon source in culture medium.

EXAMPLE 8

Relationship between NaCl Concentration and Water Absorption

In consideration of possible applications of the polysaccharide of the present invention, such as paper diapers and sanitary napkins, the retention of its water absorbing capability in the presence of sodium chloride is a very important factor for its industrial and commercial use. The synthetic high polymer absorbents in current use are capable of absorbing pure (distilled) water 200-300 times their own weight, but their ability is reduced to only 50-80 times their weight in the presence of physiological saline (0.9%). Thus, in order to verify the effectiveness of the polysaccharide of the present invention as a water absorbent, its water absorbing capability was investigated at varying NaCl concentrations and the results are shown in Table 11 below.

TABLE 11

| Relationship between NaCl Concentrations of Water Absorption | |
|---|---|
| NaCl concentration (%) | Water absorption (w/w) |
| 0 | 1439 |
| 0.25 | 612 |
| 0.5 | 579 |
| 1 | 452 |
| 2.5 | 376 |

As Table 11 shows, Biopolymer B-16 of the present invention was capable of absorbing water 450 and 370 times its own weight at NaCl concentrations of 1% and 2.5%, respectively. These values were even higher than the ability of conventional superabsorbent polymers to absorb distilled water. This feature of Biopolymer B-16 will prove to be a great advantage for its commercial use.

EXAMPLE 9

The viscosity vs concentration characteristics of the powder of polymer sample $SP_2$ prepared in Example 1 were measured. Kelzan (general-purpose xanthan gum of Kelco Co.), all particles of which passed a 28-mesh screen, was used as a control. Each sample and control was dissolved in pure water at a concentration of 1% (w/w) and thereafter diluted with pure water at varying concentrations of 0.1 to 1%. The viscosity of the respective dilutions was measured with a Brookfield type viscometer (25° C. and 30 rpm on No. 2 spindle). The results are shown in FIG. 9, from which one can see that the sample of the present invention had higher viscosities than Kelzan at all concentrations tested.

EXAMPLE 10

The physical characteristics of $SP_2$ and Kelzan in aqueous solution were measured. An aqueous solution containing 2000 ppm of SP aqueous solution containing 5000 ppm of Kelzan was prepared. The rotational speed of No. 2 spindle in a Brookfield viscometer (pH 7.2 and 25° C.) was varied between 6 rpm and 60 rpm and the resulting changes in the viscosity of each solution were measured The result for $SP_2$ is shown in FIG. 10A and that for Kelzan is shown in FIG. 10-B, from which one can see that Kelzan displayed pseudoplastic characteristics. When viscosity measurements were conducted with increasing shear rate, $SP_2$ also displayed pseudoplastic characteristics as evidenced by decreasing viscosity. When the shear rate was lowered immediately after it reached a peak, the viscosity was lower than the previous value. When shearing was stopped and the solution was left to stand, its viscosity returned to the normal level. Because of this histeresis in viscosity, SPz was found to have thixotropic characteristics.

EXAMPLE 11

Figure 11:
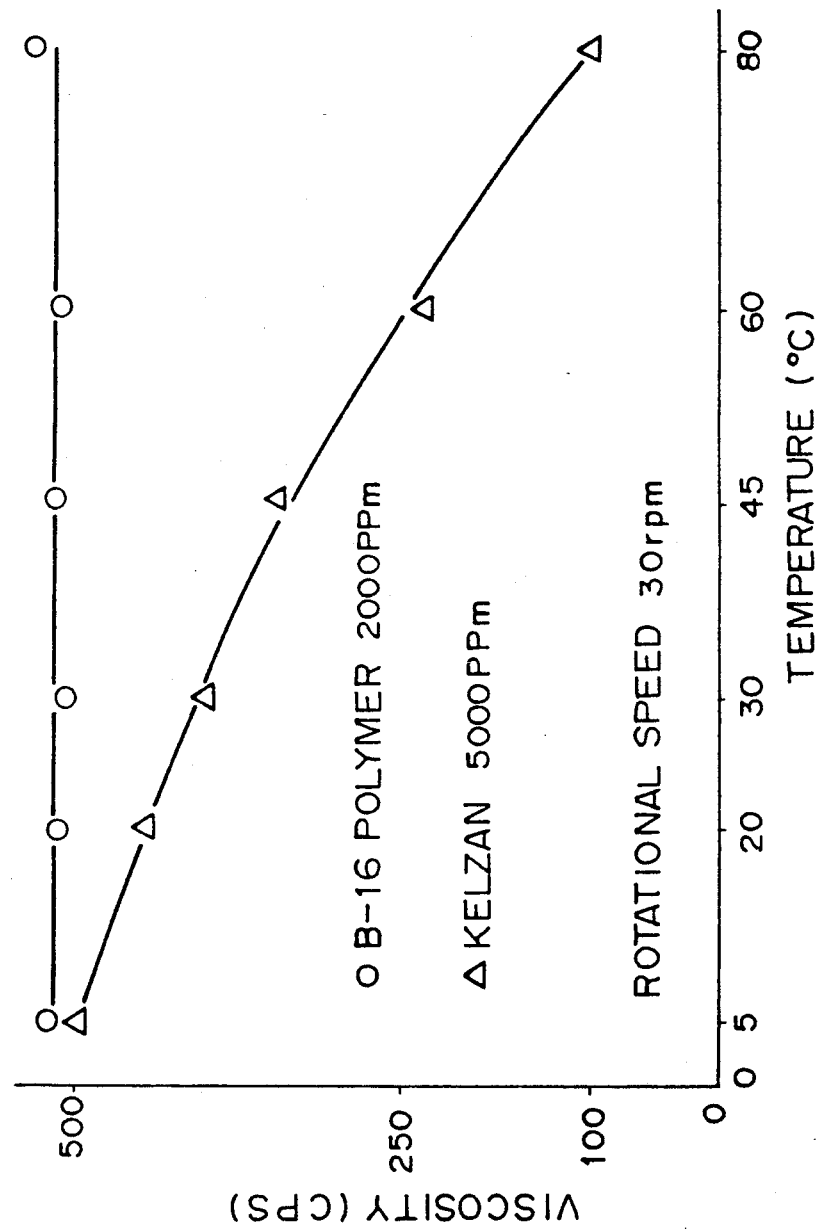
FIG. 11 is a graph showing the viscosity vs the temperature characteristics of SP$_2$ and Kelzan (control), with the vertical and horizontal axes plotting viscosity (cps) and temperature (.C), respectively.

The viscosity vs temperature characteristics of $SP_2$ were measured. An aqueous solution containing 2000 ppm of $SP_2$ and an aqueous solution containing 5000 ppm of Kelzan were prepared and their viscosity was measured with a Brookfield Viscometer (pH 7.2; rotational speed of No. 2 spindle, 30 rpm) with the temperature raised from 5° to 80° C. The results are shown in FIG. 11, from which one can see that the viscosity of $SP_2$ was substantially constant irrespective of the temperature, although the viscosity of the Kelzan decreased with temperature.

The viscosity of many synthetic and natural polymers increases with decreasing temperature and decreases with increasing temperature. Kelzan is one of the polymers known to experience minimum changes in viscosity with temperature changes, but as is clear from FIG. 11, the viscosity change was much smaller in $SP_2$ than in Kelzan.

EXAMPLE 12

Figure 12:
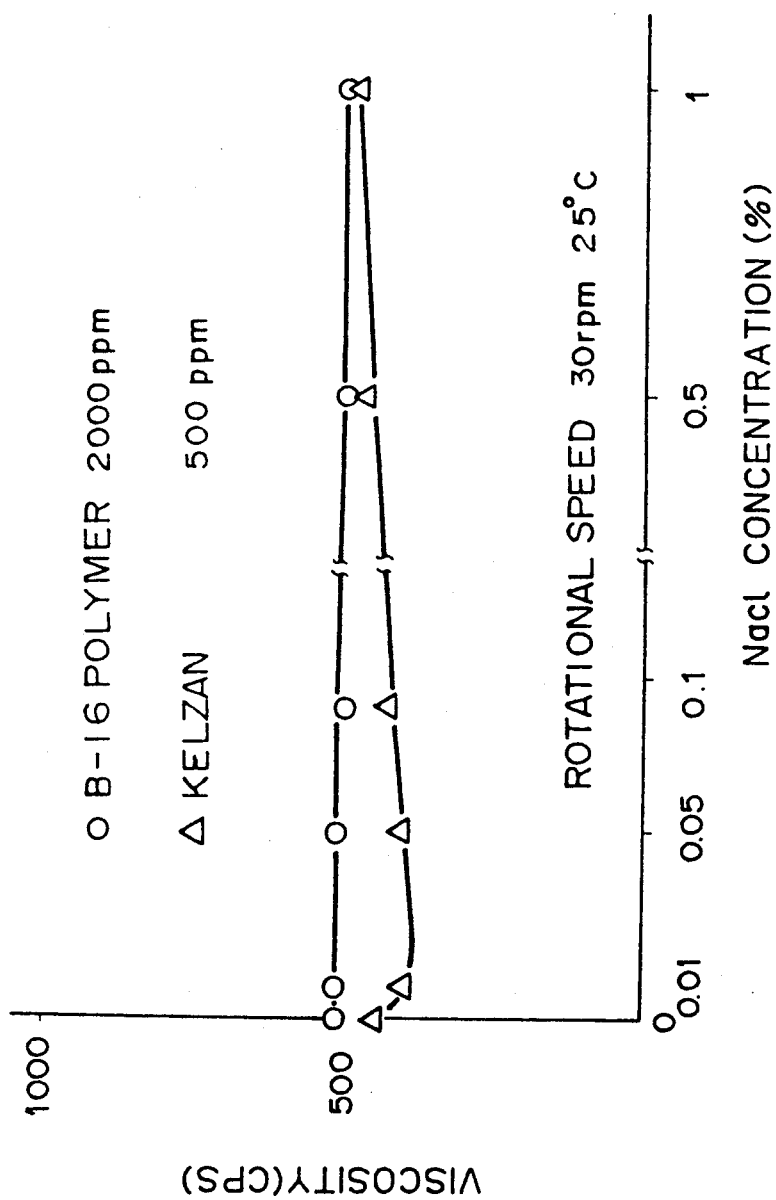
FIG. 12 is a graph showing the relationship between the concentration of NaCl in aqueous solutions of SP$_2$ and Kelzan (control) and their viscosity, with the vertical and horizontal axes plotting viscosity (cps) and the NaCl concentration (w/w %), respectively.

The relationship between the NaCl concentration of an aqueous solution containing $SP_2$ and its viscosity was measured. Sodium chloride was dissolved in pure water at concentrations of 0.01%, 0.05%, 0.1%, 0.5% and 1.0% and 2000 ppm of $SP_2$ or 5000 ppm of Kelzan was dissolved in each of the resulting NaCl solutions. Viscosity measurements were conducted with a Brookfield viscometer (25° C. and pH 7.2) with No. 2 spindle rotated at 30 rpm. The results are shown in FIG. 12, from which one can see that the viscosity of $SP_2$ was less sensitive to NaCl concentration than that of Kelzan.

EXAMPLE 13

Figure 13:
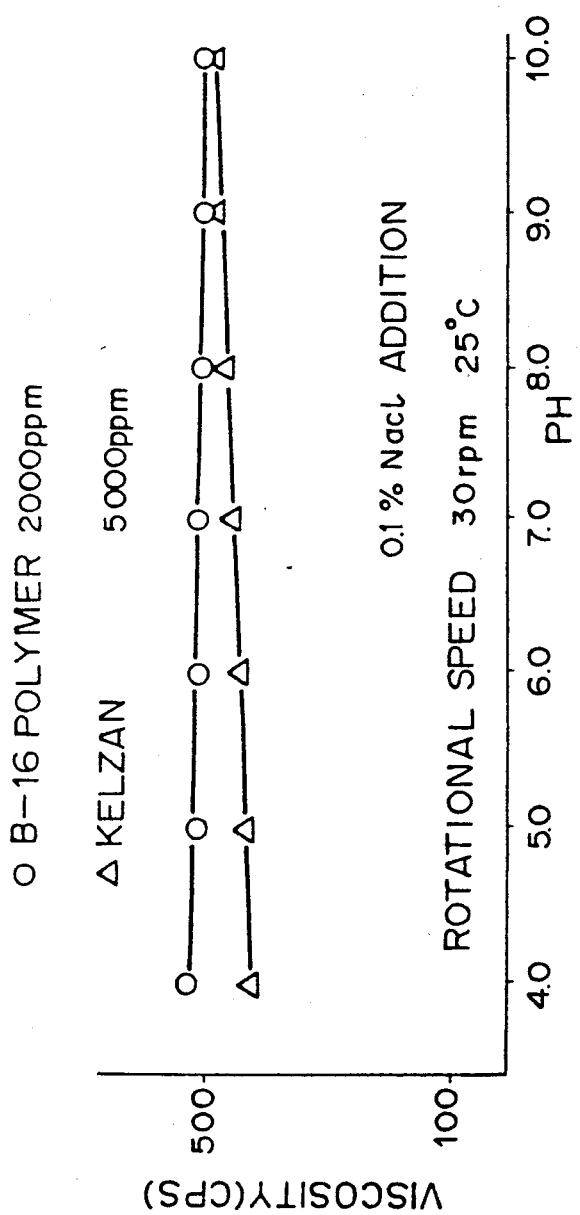
FIG. 13 is a graph showing the relationship between the pH of aqueous solutions of SP$_2$ and Kelzan (control) and their viscosity, and the vertical and horizontal axes plotting viscosity (cps) and pH, respectively.

The viscosity vs pH characteristics of $SP_2$ were measured. An aqueous solution of 0.1% NaCl was prepared and 2000 ppm of $SP_2$ or 5000 ppm of Kelzan was dissolved in this aqueous NaCl solution. After pH adjustment with HCl or NaOH, viscosity measurements were conducted with a Brookfield viscometer at 25° C. with No. 2 spindle rotating at 30 rpm. The results are shown in FIG. 13, from which one can see that SP was less sensitive to pH than Kelzan in terms of viscosity.

EXAMPLE 14

0.1 g of Biopolymer B-16 was dissolved in 100 ml of soil extract and left to stand at 30° C. for one month. After the surface of the solution had gathered mold, it was diluted to 1,000 ml with purified water and subjected to centrifuging at the rate of 20,000 G for 20 minutes with a view to removing fungi and was then further concentrated to 30 ml by means of a rotary evaporator. Ethanol, in an amount of five times that of the concentrate, was added thereto to precipitate Biopolymer B-16. The precipitate was dried at room temperature and weighed. It weighed 0.01 g.

As a control example, the same sample as referred to above was subjected to autoclaving and left to stand under sterile conditions. Therefore, the same operation as above was performed. Almost the entire amount of Biopolymer B-16 was recovered, and it weighed 0.1 g.

As is made clear by the above results, ( 10 Biopolymer B-16 was found to exhibit biodegradable.

EXAMPLE 15

A 20% suspension of cornstarch was prepared, and Biopolymer B-16, with or without 1 g of formalin (30 weight percent aqueous solution) as antiseptic, was added thereto. The resulting sample was placed in a 1 l graduated measuring cylinder and left to stand for 96 hours. The separated solid-liquid surface was measured. When Biopolymer B-16 was not added, the surface formed at the 650 ml mark of the cylinder, which meant that the separation rate was 35%. On the other hand, when 0.05% of Biopolymer B-16 was added, the separation rate was 25%. When 0.1% thereof was added, the separation rate was 0%.

As is clear from the results, Biopolymer B-16 was found to exhibit suspension stability.

EXAMPLE 16

2 g of palm oil acid were placed in 10 ml of water and the mixture was emulsified by means of a homogenizer. The emulsified sample, with or without 2 g of Biopolymer B-26, was then placed in a graduated measuring cylinder to be left to stand for 96 hours. When Biopolymer B-16 was not added, the emulsion was not retained and an oily matter was observed on the surface. On the other hand, when Biopolymer B-16 was added, the emulsion was retained.

As is clear from the above results, Biopolymer B-16 was found to exhibit emulsion stability.

EXAMPLE 17

The pasted carbon fiber reinforced concrete specified in the Table 12 given below (hereinafter referred to as CFRC) was prepared with or without Biopolymer B-16, formed in the mold (40 mm × 160 mm × 10 mm) and left to stand for 24 hours at 20° C. in a humidistat. After being taken out of the mold, it was subjected to autoclaving (180° C., 10 kg/cm, 5 hours) to obtain a CFRC board.

TABLE 12

| Raw Material | Blending (casting) Weight (g) |
|---|---|
| Standard Portland cement (manufactured by Sumitomo Cement K.K.) | 2,000 |
| No. 8 siliceous sand | 2,000 |
| Shirasu Baloon: Sanki-Light Y-04 (manufactured by Sanki Engineering Co., Ltd.) | 500 |
| Carbon fiber; pitch type 1 = 10 mm. φ = 15μ (manufactured by Kureha Chemical Id. K.K.) | 100 |
| City water | 2,500 |
| Biopolymer B-16 | 10 |

When Biopolymer B-16 was not added, the strength of the resulting CFRC board was 3 kgf/cm$^2$. On the other hand, when Biopolymer B-16 was added, the strength thereof was greatly increased to 173 kgf/cm$^2$.

As is clear from the above results, Biopolymer B-16 was found to exhibit dispersant capability.

In addition to the field of cosmetics, the sanitary industry, paper diapers and greening desert, the following are examples of the applications in which Biopolymer B-16 of the present invention may be put to use:

Food applications:
Thickeners, fillers, water retainers, texture improving agents, dietary foods;

Feedstuff applications:
Thickeners, fillers, water retainers, carrier entrapping;

Medical applications:
Immunoactivators, drug entrapping (e.g., capsules and tablets);

Biotechnological applications:
Immobilizers for use in bioreactors, etc., culture bases for microorganisms, plants and animal cells, supports (gels) for separation and purification;

Agricultural application:
Capsules of slow release agents (e.g., agrichemicals), suspension stabilizers, emulsion stabilizers, improving adhesion, improving dustability, controlling the shape of liquid droplets;

Civil engineering:
Soil improving agents, soil water retainers, mud stabilizers, soil stabilizers;

Distribution:
Drip absorbents for use in foods such as fish and meat;

Paper coating:
Improving the performance of coatings, preventing migration, preventing streaks, preventing pigment sedimentation, improving water retention;

Textile dyeing:
Preventing pigment sedimentation, preventing migration, improving dye fluidity, space dyeing;

Latices:
Emulsion stabilizers;

Cleaners:
Emulsion stabilizers, suspension stabilizers, anti-sagging agents, improving sprayability;

Foam stabilizers:
Stabilizing TiO$_2$ suspensions, stabilizing the suspensions of starch slurry;

Foam stabilizers:
Foamed cement;

Improvement of polishing agents:
Buffing agents;

Paint improving agents:
Improving rheological properties.

What is claimed is:

1. A polysaccharide being produced by cultivating Alcaligenes latus strain B-16 (FERM-2015) and having the following properties:

(A) sugar composition as determined by thin-layer chromatography, liquid chromatography and gas chromatography:
   the principal constituents are rhamnose, fucose, glucose, mannose and glucuronic acid which are present in a molar ratio of (1–10):(2–10):(4–20):(1):(1–5), respectively;

(B) elemental analysis (weight percent):

| | |
   |---|---|
   | C: | 40 ± 4 |
   | H: | 6 ± 1 |
   | O: | 54 ± 5; |

(C) carbonization point: 225°–280° C.;
   (D) solubility:
   slightly soluble in water (neutral); soluble in alkalies; insoluble in methanol, ethanol and acetone;
   (E) UV absorption spectrum:
   no absorption detected at 280 nm characteristic of proteins (peptides) or at 260 nm characteristic of nucleic acids; and
   (F) IR absorption spectrum;
   having peaks at 800–1200 cm$^{-1}$, 1620±20 cm$^{-1}$, 2950±10 cm$^{-1}$ and 3400 ±20 cm$^{-1}$.

2. A polysaccharide according to claim 1 which contains 5–20 mol% glucuronic acid, with rhamnose, fucose, glucose and mannose being present in a molar ratio of (1–6):(3–5):(5–17):(1), respectively.

3. A polysaccharide according to claim 1 which contains rhamnose, fucose, glucose, mannose and glucuronic acid in a molar ratio of (1–3):(3–5): (5–7):(1):(2–3), respectively.

* * * * *

UNITED STATES PATENT AND TRADEMARK OFFICE
CERTIFICATE OF CORRECTION

PATENT NO. : 5,175,279

DATED : December 29, 1992

INVENTOR(S) : Ryuichiro Kurane, et al

It is certified that error appears in the above-identified patent and that said Letters Patent is hereby corrected as shown below:

Column 1, line 14, change "*Alcalioenes*" to --*Alcaligenes*--.

Column 3, line 50, change "Alcalioenes latus" to --*Alcaligenes latus*--.

Column 3, line 63, change "(.C)" to --(°C)--.

Column 4, line 18, change "Alcaligenes" to "*Alcaligenes*".

Column 4, line 58, after "10" insert a comma.

Column 4, lines 60 and 61, change "Alcaligenes latus" to "*Alcaligenes latus*".

Column 6, line 53, insert --Percentage of moisture absorption--.

Column 7, lines 3 and 4, delete the extra space between "100 mg" and "in".

Column 7, line 38, change "*Alcalioenes*" to --*Alcaligenes*--.

UNITED STATES PATENT AND TRADEMARK OFFICE
CERTIFICATE OF CORRECTION

PATENT NO. : 5,175,279

DATED : December 29, 1992

INVENTOR(S) : Ryuichiro Kurane et al.

It is certified that error appears in the above-identified patent and that said Letters Patent is hereby corrected as shown below:

Column 8, line 23, begin a paragraph with "(5) UV absorption spectrum:".

Column 10, line 43, in the column heading, after "solvent c" change the period to a comma.

Column 14, line 34, delete the extra space between "glucuronic" and "acid".

Column 14, line 39, in the subheading, delete the blank line.

Column 16, lines 33 and 34, change "use din" to --used in--.

Column 16, line 54, change "SPz" to --$SP_2$--.

Column 16, line 58, change "SPz" to --$SP_2$--.

Column 17, line 37, change "SPz" to --$SP_2$--.

UNITED STATES PATENT AND TRADEMARK OFFICE
CERTIFICATE OF CORRECTION

PATENT NO. : 5,175,279
DATED : December 29, 1992
INVENTOR(S) : Ryuichiro KURANE et al.

It is certified that error appears in the above-identified patent and that said Letters Patent is hereby corrected as shown below:

Column 18, line 27, change "SPz" to --SP$_2$--.

Column 18, line 37, change "g/l" to --g/ℓ--.

Column 19, line 44, after "measured" insert a period.

Column 19, line 54, change "SPz" to --SP$_2$--.

Column 20, line 51, delete "(10".

Column 20, line 58, change "1 1" to --1 ℓ--.

Column 21, line 19, change "B-16,formed" to --B-16, formed--.

Column 21, line 32, after "type" change "1" to --ℓ--.

Signed and Sealed this

Eighteenth Day of January, 1994

Attest:

BRUCE LEHMAN

*Attesting Officer*   *Commissioner of Patents and Trademarks*